(12) United States Patent
Shelby et al.

(10) Patent No.: US 12,721,928 B1
(45) Date of Patent: Sep. 1, 2026

(54) ACTIVE AGENT-ELUTING HEMOSTATIC AGENTS FOR PREVENTION OF SURGICAL SITE INFECTION

(71) Applicant: Florida Southern College, Lakeland, FL (US)

(72) Inventors: Shameka J. Shelby, Auburndale, FL (US); Zachary D. Fralish, Niceville, FL (US); Keith R. Berend, New Albany, OH (US)

(73) Assignee: Florida Southern College, Lakeland, FL (US)

(*) Notice: Subject to any disclaimer, the term of this patent is extended or adjusted under 35 U.S.C. 154(b) by 0 days.

(21) Appl. No.: 18/219,400

(22) Filed: Jul. 7, 2023

Related U.S. Application Data

(62) Division of application No. 17/242,219, filed on Apr. 27, 2021, now Pat. No. 12,397,083.
(Continued)

(51) Int. Cl.

| | |
|---|---|
| ***A61K 47/42*** | (2017.01) |
| ***A61K 31/192*** | (2006.01) |
| ***A61K 31/235*** | (2006.01) |
| ***A61K 38/14*** | (2006.01) |
| ***A61K 45/06*** | (2006.01) |
| ***A61K 47/36*** | (2006.01) |

(Continued)

(52) U.S. Cl.
CPC ....... *A61L 26/0066* (2013.01); *A61L 26/0038* (2013.01); *A61L 2300/406* (2013.01); *A61L 2300/602* (2013.01); *A61L 2400/04* (2013.01)

(58) Field of Classification Search
CPC ............ A61L 26/0066; A61L 26/0038; A61L 2300/602; A61L 2300/406; A61L 2400/04
See application file for complete search history.

(56) References Cited

U.S. PATENT DOCUMENTS 7,282,220 B1 * 10/2007 Sung .................... A61K 9/0019 424/501
9,833,541 B2 * 12/2017 McCoy ................. A61L 24/108
(Continued)

FOREIGN PATENT DOCUMENTS

WO WO 2003/007845 * 1/2003

OTHER PUBLICATIONS

Yasmin et al.: Gelatin nanoparticles: a potential candidate for medical applications, Nanotechnology Reviews, 2017, 6(2), 191-207 (Year: 2016).*

(Continued)

*Primary Examiner* — Hong Yu
(74) *Attorney, Agent, or Firm* — Michele L. Lawson; Shumaker, Loop & Kendrick, LLP

(57) ABSTRACT

A novel active agent-eluting hemostatic agent and methods of use and manufacture thereof are presented. A polymer, such as gelatin, is used as the base for a hemostatic agent. The gelatin is crosslinked with a chemical crosslinker, such as a carbodiimide, in the presence of an active agent. The active agent may be an anesthetic or antimicrobial, such as an antibiotic. The novel process allows for the active agent to be both covalently bound to the gelatin as well as be trapped within cages in the gelatin that are formed from the crosslinking. This dual measure allows for controlled and sustained release of the active agent from the hemostatic agent to reduce surgical site infections.

12 Claims, 16 Drawing Sheets

Related U.S. Application Data

(60) Provisional application No. 63/016,621, filed on Apr. 28, 2020.

(51) Int. Cl.
*A61L 26/00* (2006.01)
*A61P 35/00* (2006.01)

(56) References Cited

U.S. PATENT DOCUMENTS

2010/0063459 A1* 3/2010 Preiss-Bloom ..... A61L 26/0047 424/94.6
2020/0276362 A1* 9/2020 Tomer ..................... A61L 27/46

OTHER PUBLICATIONS

Cammarata et al.: Carbodiimide Induced Cross-Linking, Ligand Addition, and Degradation in Gelatin, Molecular Pharmaceutics vol. 12/Issue 3, Feb. 6, 2015, p. 783-793 (Year: 2015).*
Chen et al.: Covalently antibacterial alginate-chitosan hydrogel dressing integrated gelatin microspheres containing tetracycline hydrochloride for wound healing, Materials Science and Engineering: C, vol. 70, Part 1, Jan. 1, 2017, pp. 287-295 (Year: 2017).*
Lin Li, et al., Preparation and the hemostatic property study of porous gelatin microspheres both in vitro and in vivo, Colloids and Surfaces B: Biointerfaces, Whole document.
Yasmin, R. et al. Gelatin nanoparticles: a potential candidate for medical applications. Nanotechnol Rev 2017; 6(2):191-207.

* cited by examiner a)

Gelatin

R =

Vancomycin

Daptomycin b)

Gelatin

R =

Vancomycin

Daptomycin

FIG. 1A-B

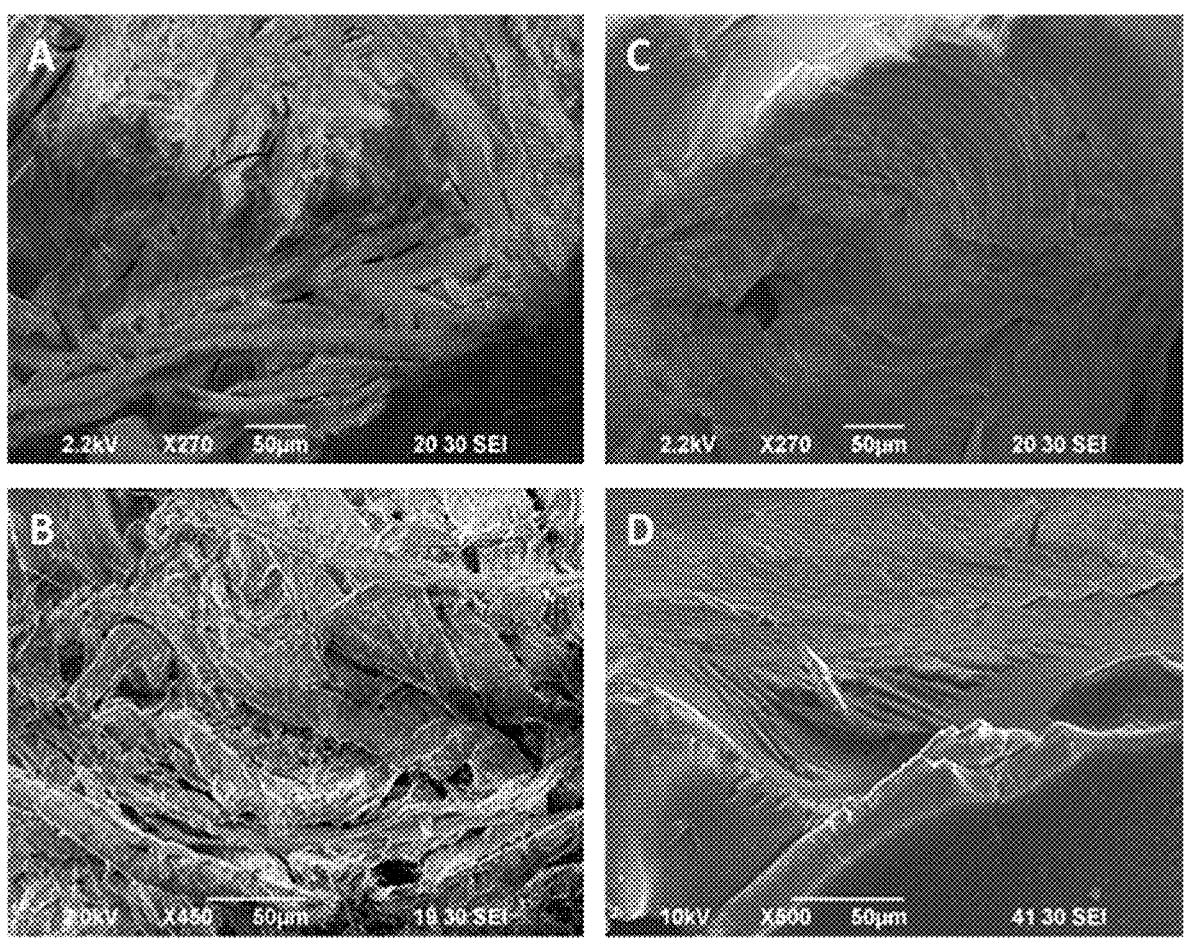
FIG. 2A-D

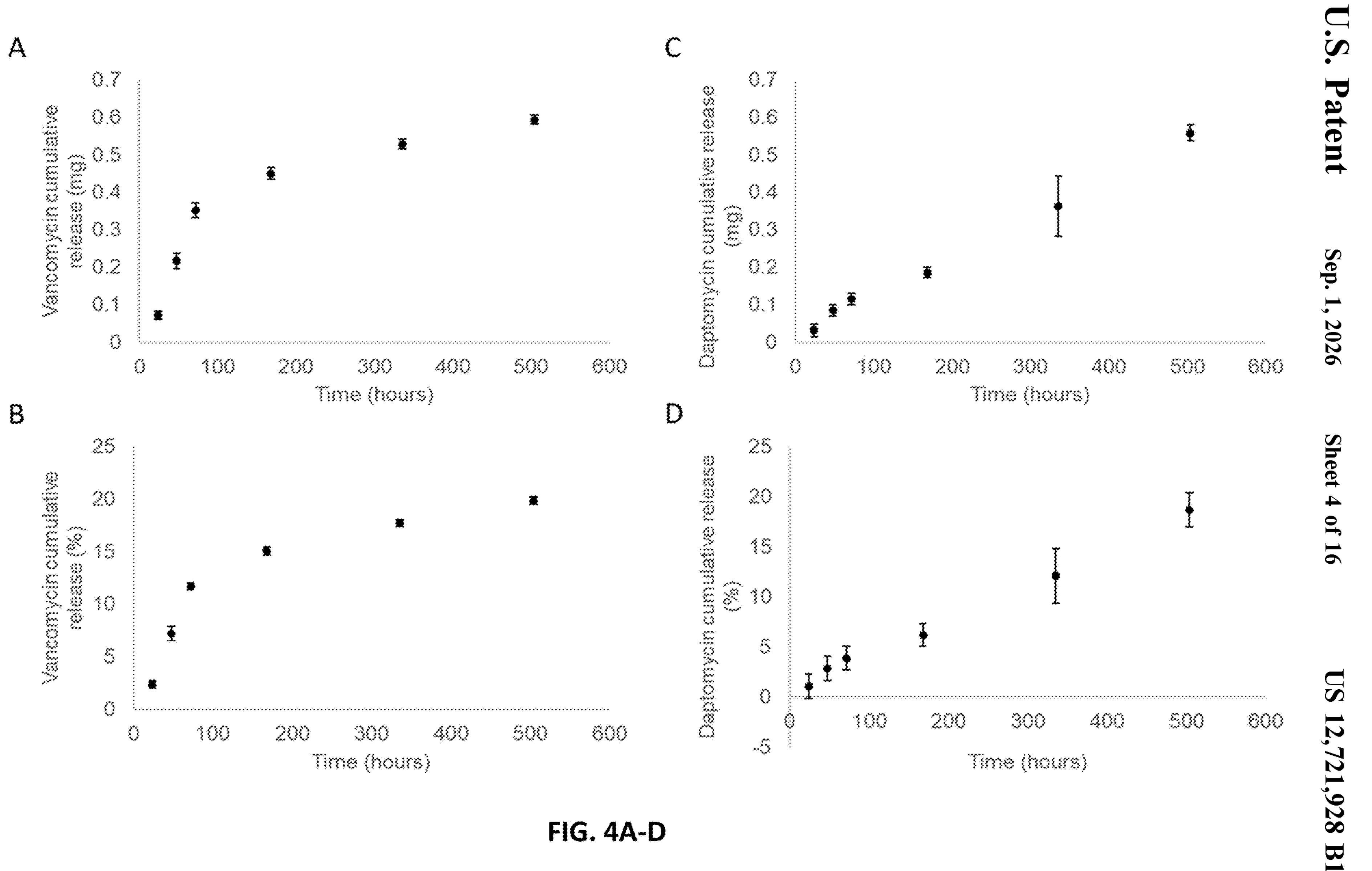
FIG. 4A-D

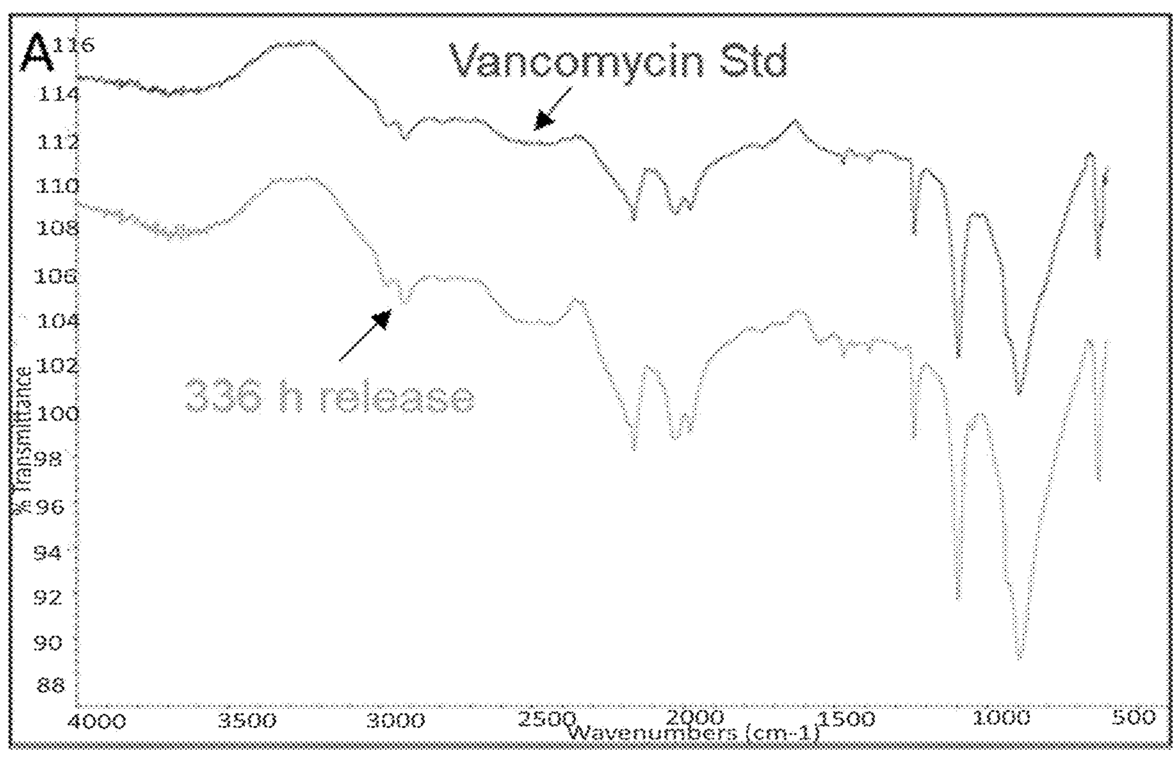
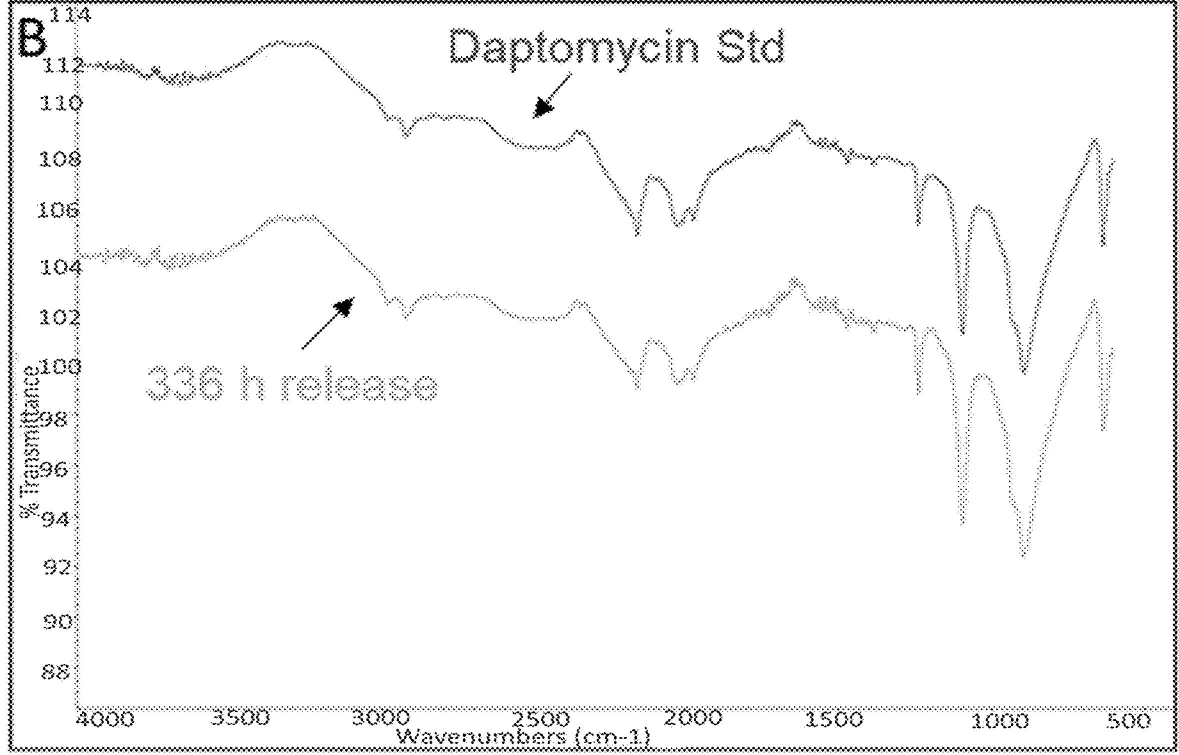
FIG. 5A-B

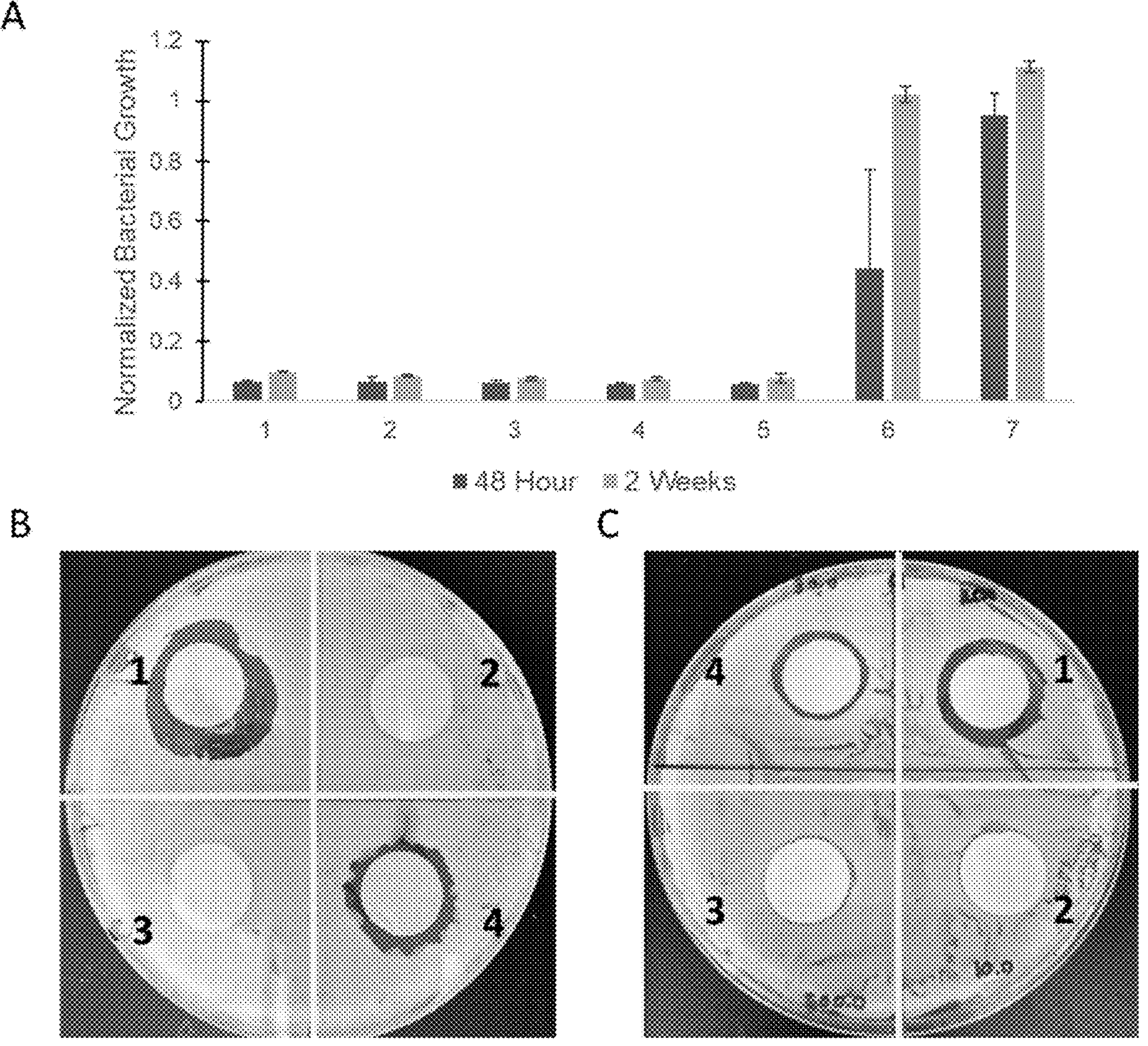
FIG. 6A-C

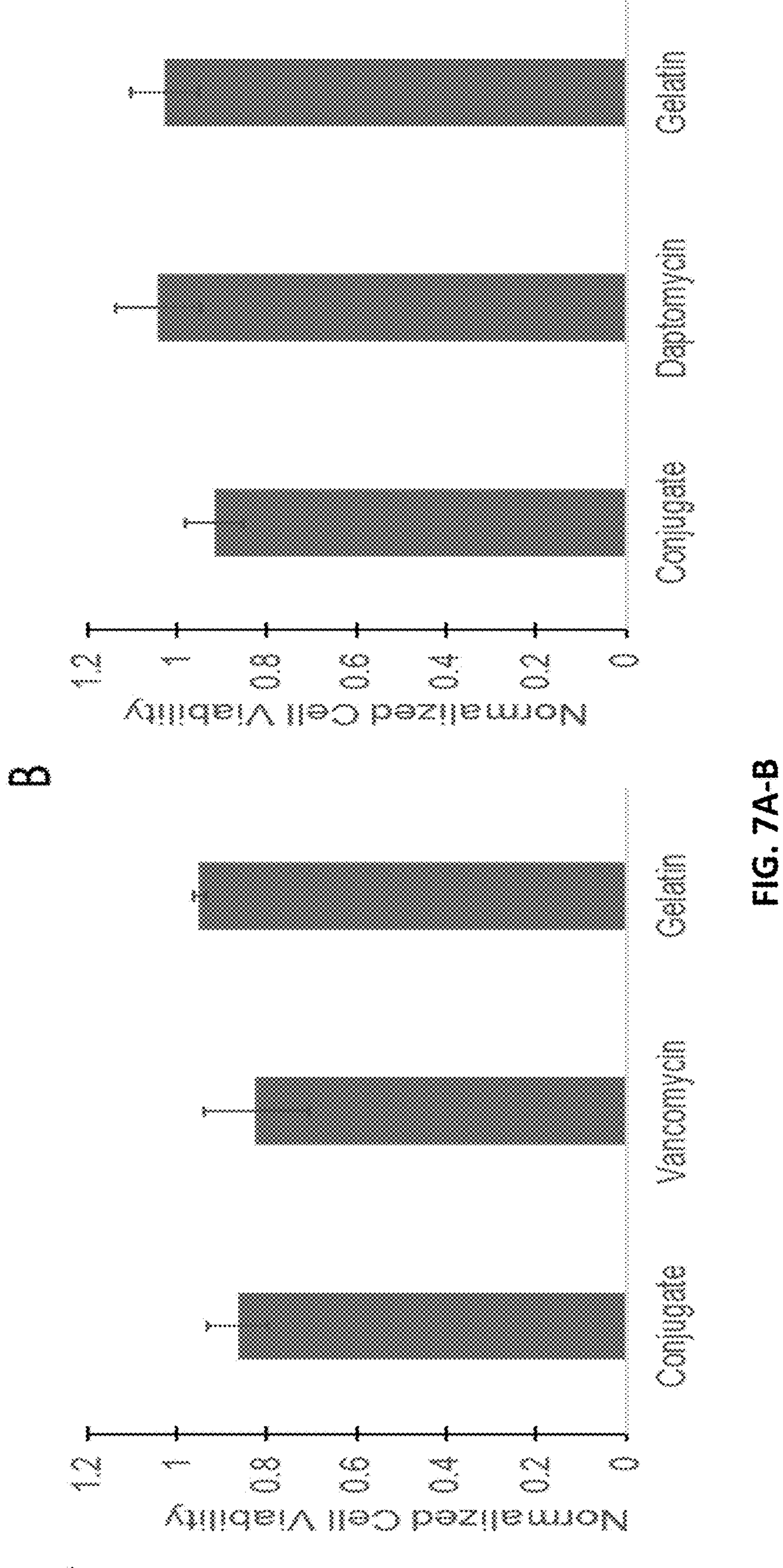
FIG. 7A-B

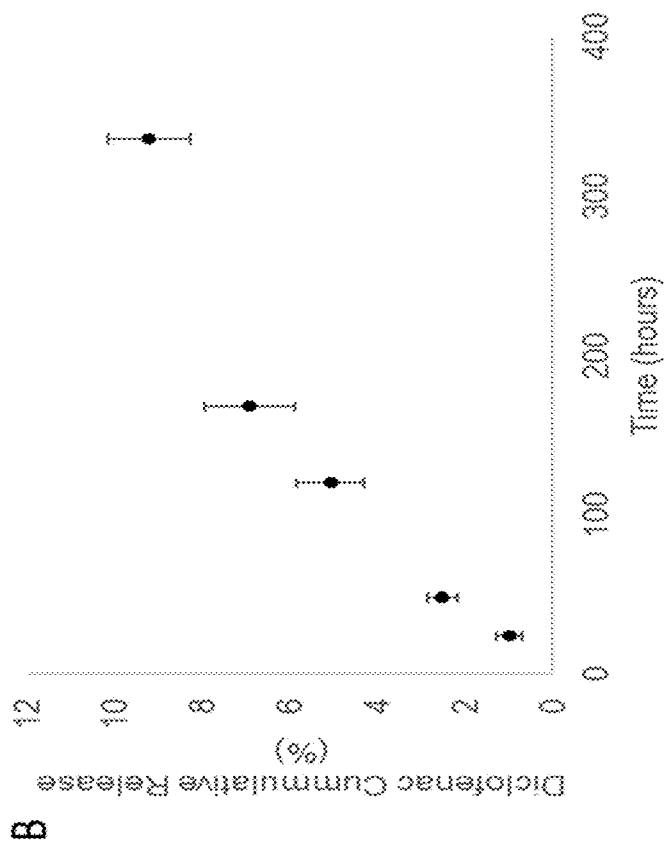
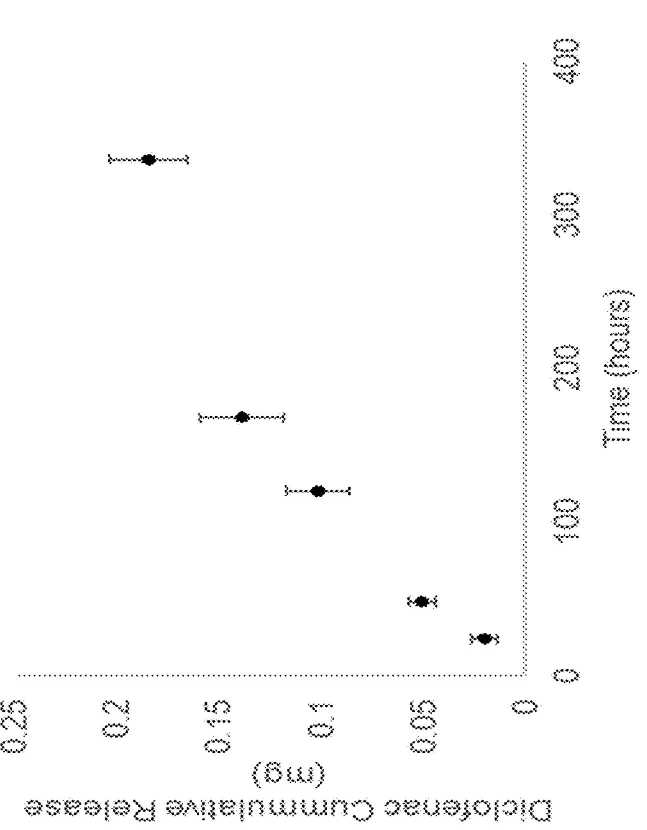
FIG. 16A-B

ACTIVE AGENT-ELUTING HEMOSTATIC AGENTS FOR PREVENTION OF SURGICAL SITE INFECTION

CROSS REFERENCE TO RELATED APPLICATIONS

This application is a divisional of and claims priority to currently pending U.S. patent application Ser. No. 17/242,219, entitled "Active Agent-Eluting Hemostatic Agents for Prevention of Surgical Site Infection", filed Apr. 27, 2021, which is a nonprovisional of and claims priority to U.S. Provisional Application No. 63/016,621 entitled "Antibiotic-Eluting Agents for Prevention of Surgical Site Infection", filed Apr. 28, 2020, the contents of each of which are hereby incorporated by reference into this disclosure.

FIELD OF INVENTION

This invention relates to hemostatic agents. Specifically, the invention provides novel anesthetic and antimicrobial-eluting hemostatic agents and methods of use thereof.

BACKGROUND OF THE INVENTION

Surgical site infections (SSIs) are a major concern in the healthcare industry that lead to lengthened hospital stays, additional surgical procedures, prolonged antibiotic use, and increased patient morbidity. (Herwaldt, L. A.; Cullen, J. J.; Scholz, D.; French, P.; Zimmerman, M. B.; Pfaller, M. A.; Wenzel, R. P.; Perl, T. M., A prospective study of outcomes, healthcare resource utilization, and costs associated with postoperative nosocomial infections. *Infect Control Hosp Epidemiol* 2006, 27 (12), 1291-8; Pull ter Gunne, A. F.; Cohen, D. B., Incidence, prevalence, and analysis of risk factors for surgical site infection following adult spinal surgery. *Spine* (Phila Pa 1976) 2009, 34 (13), 1422-8).

Although infections are often remitted, they increase medical costs and reduce functional prognosis of patients after surgery. (Calderone, R. R.; Garland, D. E.; Capen, D. A.; Oster, H., Cost of medical care for postoperative spinal infections. *Orthop Clin North Am* 1996, 27 (1), 171-82; Petilon, J. M.; Glassman, S. D.; Dimar, J. R.; Carreon, L. Y., Clinical outcomes after lumbar fusion complicated by deep wound infection: a case-control study. *Spine* (Phila Pa 1976) 2012, 37 (16), 1370-4; Chen, S. H.; Lee, C. H.; Huang, K. C.; Hsieh, P. H.; Tsai, S. Y., Postoperative wound infection after posterior spinal instrumentation: analysis of long-term treatment outcomes. *Eur Spine J* 2015, 24 (3), 561-70). It is estimated that SSIs occur during 2% to 13% of spinal surgeries and periprosthetic joint infections will occur in up to 80,000 patients per year in the United States by 2030 creating a cost burden up to $4 billion annually. (Kurtz, S. M.; Lau, E.; Watson, H.; Schmier, J. K.; Parvizi, J., Economic burden of periprosthetic joint infection in the United States. *J Arthroplasty* 2012, 27 (8 Suppl), 61-5 el; Parvizi, J.; Pawasarat, I. M.; Azzam, K. A.; Joshi, A.; Hansen, E. N.; Bozic, K. J., Periprosthetic joint infection: the economic impact of methicillin-resistant infections. *J Arthroplasty* 2010, 25 (6 Suppl), 103-7; Rechtine, G. R.; Bono, P. L.; Cahill, D.; Bolesta, M. J.; Chrin, A. M., Postoperative wound infection after instrumentation of thoracic and lumbar fractures. *J Orthop Trauma* 2001, 15 (8), 566-9)

Several preventative methods have been considered effective in preventing SSIs including surgical hand preparations, post-discharge surveillance, postponing elective surgeries in the case of an existing infection, and antimicrobial prophylaxis. (Parvizi, J.; Pawasarat, I. M.; Azzam, K. A.; Joshi, A.; Hansen, E. N.; Bozic, K. J., Periprosthetic joint infection: the economic impact of methicillin-resistant infections. *J Arthroplasty* 2010, 25 (6 Suppl), 103-7; Owens, C. D.; Stoessel, K., Surgical site infections: epidemiology, microbiology and prevention. *J Hosp Infect* 2008, 70 Suppl 2, 3-10). Antimicrobial prophylaxis has become standard practice after orthopedic surgery. (Pull ter Gunne, A. F.; Cohen, D. B., Incidence, prevalence, and analysis of risk factors for surgical site infection following adult spinal surgery. *Spine* (Phila Pa 1976) 2009, 34 (13), 1422-8.; Rechtine, G. R.; Bono, P. L.; Cahill, D.; Bolesta, M. J.; Chrin, A. M., Postoperative wound infection after instrumentation of thoracic and lumbar fractures. *J Orthop Trauma* 2001, 15 (8), 566-9; Devin, C. J.; Chotai, S.; McGirt, M. J.; Vaccaro, A. R.; Youssef, J. A.; Orndorff, D. G.; Arnold, P. M.; Frempong-Boadu, A. K.; Lieberman, I. H.; Branch, C.; Hedayat, H. S.; Liu, A.; Wang, J. C.; Isaacs, R. E.; Radcliff, K. E.; Patt, J. C.; Archer, K. R., Intrawound Vancomycin Decreases the Risk of Surgical Site Infection After Posterior Spine Surgery: A Multicenter Analysis. *Spine* (Phila Pa 1976) 2018, 43 (1), 65-71). Cefazolin and other cephalosporins are considered sufficient to be used in antimicrobial prophylaxis to target *Staphylococcus aureus*. (Epstein, N. E., Preoperative measures to prevent/minimize risk of surgical site infection in spinal surgery. *Surg Neurol Int* 2018, 9, 251; Noskin, G. A.; Rubin, R. J.; Schentag, J. J.; Kluytmans, J.; Hedblom, E. C.; Jacobson, C.; Smulders, M.; Gemmen, E.; Bharmal, M., National trends in *Staphylococcus aureus* infection rates: impact on economic burden and mortality over a 6-year period (1998-2003). *Clin Infect Dis* 2007, 45 (9), 1132-40). However, due to increased rates of MRSA induced SSI, vancomycin and other glycopeptides/lipopeptides including daptomycin have been more widely used.

Alongside antibiotics, hemostatic agents are considered almost mandatory following orthopedic surgery. Gelatin began replacing clips, electrocoagulation, and ligature to obtain hemostasis in the 1940's and has been widely used ever since due to its biodegradability and biocompatibility. (Green, D.; Wong, C. A.; Twardowski, P., Efficacy of hemostatic agents in improving surgical hemostasis. *Transfus Med Rev* 1996, 10 (3), 171-82; Jenkins, H. P.; Clarke, J. S., Gelatin sponge, a new hemostatic substance; studies on absorbability. *Arch Surg* 1945, 51, 253-61). Despite variations in compositions and structures across gelatins, consistently high levels of crosslinking throughout gelatins allows them to function as dependable hemostatic agents. (Olsen, D.; Yang, C.; Bodo, M.; Chang, R.; Leigh, S.; Baez, J.; Carmichael, D.; Perala, M.; Hamalainen, E. R.; Jarvinen, M.; Polarek, J., Recombinant collagen and gelatin for drug delivery. *Adv Drug Deliv Rev* 2003, 55 (12), 1547-67). The high content of amino acids such as glycine, proline, and hydroxyproline function to potentially accelerate the healing of soft tissue. (Tanaka, A.; Nagate, T.; Matsuda, H., Acceleration of wound healing by gelatin film dressings with epidermal growth factor. *J Vet* Med Sci 2005, 67 (9), 909-13). The highly hydrophilic nature of gelatin allows for drug absorption in the form of a hydrogel and controlled drug release through a degradation or diffusion-controlled mechanism. (Ikada, Y.; Tabata, Y., Protein release from gelatin matrices. *Adv Drug Deliv Rev* 1998, 31 (3), 287-301).

The current push for antibiotic-eluting devices to proactively prevent infections can be found throughout recent literature. (Gimeno, M.; Pinczowski, P.; Mendoza, G.; Asin, J.; Vazquez, F. J.; Vispe, E.; Garcia-Alvarez, F.; Perez, M.; Santamaria, J.; Arruebo, M.; Lujan, L., Antibiotic-eluting orthopedic device to prevent early implant associated infections: Efficacy, biocompatibility and biodistribution studies in an ovine model. *J Biomed Mater Res B Appl Biomater* 2018, 106 (5), 1976-1986). Studies have produced gelatin-based bandages, sponges, and hydrogels that release antibiotic over approximately 7 days. (Shefy-Peleg, A. F., M.; Cohen, B.; Zilberman, M., Novel antibiotic-eluting gelatin-alginate soft tissue adhesives for various wound closing applications. *International Journal of Polymeric Materials and Polymeric Biomaterials* 2014, 63 (14), 699-707; Shukla, A.; Fang, J. C.; Puranam, S.; Hammond, P. T., Release of vancomycin from multilayer coated absorbent gelatin sponges. *J Control Release* 2012, 157 (1), 64-71). Alternatively, gelatin sponges incorporating varying concentrations of 0-tricalcium phosphate ceramic (0-TCP) have been developed to function as a vancomycin sustained-release system in the treatment of chronic osteomyelitis. (Zhou, J.; Fang, T.; Wang, Y.; Dong, J., The controlled release of vancomycin in gelatin/0-TCP composite scaffolds. *Journal of biomedical materials research Part A* 2012, 100 (9), 2295-2301). Also, many successful surgeries have incorporated antibiotic-infused bone cement during bone replacement surgeries. (Gandhi, R.; Backstein, D.; Zywiel, M. G., Antibiotic-laden Bone Cement in Primary and Revision Hip and Knee Arthroplasty. *J Am Acad Orthop Surg* 2018, 26 (20), 727-734; Stravinskas, M.; Nilsson, M.; Horstmann, P.; Petersen, M. M.; Tarasevicius, S.; Lidgren, L., Antibiotic Containing Bone Substitute in Major Hip Surgery: A Long Term Gentamicin Elution Study. *J Bone Jt Infect* 2018, 3 (2), 68-72). Treatments with bone cement were assessed as efficacious and well tolerated for all patients, indicating the effectiveness of the combination of antibiotics with internal agents. (Kendoff, D. O.; Gehrke, T.; Stangenberg, P.; Frommelt, L.; Bosebeck, H., Bioavailability of gentamicin and vancomycin released from an antibiotic containing bone cement in patients undergoing a septic one-stage total hip arthroplasty (THA) revision: a monocentric open clinical trial. *Hip Int* 2016, 26 (1), 90-6).

In addition to bioadhesive applications, gelatin conjugates have been studied as anti-cancer agents. Protocols have been established for conjugating doxorubicin and methotrexate to gelatin. (Ofner, C. M., 3rd; Pica, K.; Bowman, B. J.; Chen, C. S., Growth inhibition, drug load, and degradation studies of gelatin/methotrexate conjugates. *Int J Pharm* 2006, 308 (1-2), 90-9; Kosasih, A. B., B. J.; Wigent, R. J.; & Ofner III, C. M., Characterization and in vitro release of methotrexate from gelatin/methotrexate conjugates formed using different preparation variables. *International Journal of Pharmaceutics* 2000, 204 (1), 81-89; Cammarata, C. R.; Hughes, M. E.; Ofner, C. M., 3rd, Carbodiimide induced crosslinking, ligand addition, and degradation in gelatin. *Mol Pharm* 2015, 12 (3), 783-93). Utilizing 1-ethyl-3-(diaminopropyl) carbodiimide HCl (EDC) as a carboxyl activating agent in peptide bond formation, methotrexate was successfully conjugated to gelatin of various molecular weights EDC-catalyzed conjugations and crosslinking reactions produce an amide bond between carboxyl and amino moieties through a carboxylic anhydride mechanism recognized to occur extensively under aqueous conditions. (Nakajima, N.; Ikada, Y., Mechanism of amide formation by carbodiimide for bioconjugation in aqueous media. *Bioconjug Chem* 1995, 6 (1), 123-30). These examples exemplify the simplicity and efficiency of peptide bond formation in direct conjugation of small molecules to gelatin.

To limit the prevalence of SSIs, there is a great need to produce highly effective and biocompatible antimicrobial prophylaxis. Effectively combining antibiotics and hemostatic agents should increase antimicrobial presence within surgical sites and improve the efficacy of antimicrobial prophylaxis. In addition, local application can reduce unnecessary systemic administration. This prevents the death of beneficial bacteria within patients and limits selection for antibiotic-resistant bacteria through the reduction of antibiotic application area. Non-steroidal anti-inflammatory drugs (NSAIDs) can also be conjugated to the hemostatic agents herein to provide an anti-inflammatory and anesthetic effect after surgery. Accordingly, what is needed is a biodegradable hemostatic agent that is capable of both immediate and sustained release of antibiotics and other active agents.

SUMMARY OF INVENTION

The inventors have combined antibiotics with gelatin through peptide bond formation via EDC to form an antibiotic-eluting hemostatic agent. This approach allowed for the direct conjugation of antibiotics to gelatin in addition to trapping of these antibiotics within crosslinked gelatin cages for use as antibiotic-releasing hemostatic agents.

The glycopeptide vancomycin and the lipopeptide daptomycin were tested along with the cephalosporins, ceftazidime and ceftibuten, and the fluoroquinolone ciprofloxacin. The NSAID diclofenac was also tested. Release profiles were analyzed from samples of various reactant ratios to optimize reaction conditions and antibacterial activity and structural integrity of eluted antibiotics was confirmed. The biocompatibility and structural makeup of the conjugations were additionally determined.

The inventors found that they were able to produce crosslinked gelatin hemostatic agents in which the antibiotic or NSAID was both bound to the gelatin itself as well as being trapped within cages formed in the crosslinked gelatin. The "free" antibiotic or NSAID that is in the cages released quicker than the antibiotic that is covalently bound to the gelatin itself thus allowing for a controlled sustained release of antibiotic over a period of at least 3 weeks and controlled release of the NSAID for at least 2 weeks.

In an embodiment, an active agent-eluting hemostatic agent is presented comprising at least one active agent conjugated to and entrapped within cages formed in a crosslinked gelatin. The active agent has at least one amine or carboxylate group in its structure and may be conjugated to the crosslinked gelatin by amide bond formation between the active agent and the gelatin. The hemostatic agent achieves both immediate and controlled sustained release of the active agent. The gelatin may be crosslinked by a chemical crosslinker selected from the group consisting of 1-ethyl-3-(3-dimethylaminopropyl) carbodiimide (EDC) and dicyclohexylcarbodiimide (DCC), and carbonyldiimidazole (CDI). In some embodiments, the crosslinking agent is EDC.

The at least one active agent may be an anesthetic, an antimicrobial, or combinations thereof. In embodiments in which the at least one active agent is an antimicrobial, the antimicrobial may be an antibiotic selected from the group consisting of glycopeptide antibiotics, lipopeptide antibiotics, quinolones, and cephalosporins. Specifically, the antibiotic may be selected from the group consisting of vancomycin, daptomycin, ciprofloxacin, ceftazidime, and ceftibuten.

In alternate embodiments, the at least one active agent may be an anesthetic such as a non-steroidal anti-inflammatory drug (NSAID). The NSAID may be selected from the group consisting of aspirin, ibuprofen, naproxen and naproxen sodium, diclofenac, oxaprozin, etodolac, indomethacin, ketolorac, and vimovo.

In a further embodiment, a method of preventing surgical site infection is presented comprising applying a therapeutically effective amount of an antimicrobial-eluting hemostatic agent to the surgical site. The antimicrobial-eluting hemostatic agent may comprise an antimicrobial conjugated to and entrapped within cages formed in a crosslinked gelatin. The antimicrobial has at least one amine or carboxylate group in its structure and may be conjugated to the crosslinked gelatin by amide bond formation between the antimicrobial and the gelatin. The hemostatic agent releases the antimicrobial in cages first followed by controlled sustained release over a period of time of the antimicrobial conjugated to the gelatin to prevent surgical site infection. The gelatin may be crosslinked by a chemical crosslinker selected from the group consisting of 1-ethyl-3-(3-dimethylaminopropyl) carbodiimide (EDC) and dicyclohexylcarbodiimide (DCC), and carbonyldiimidazole (CDI). In some embodiments, the crosslinking agent is EDC.

In some embodiments, the antimicrobial is an antibiotic selected from the group consisting of glycopeptide antibiotics, lipopeptide antibiotics, quinolones, and cephalosporins. Specifically, the antibiotic may be selected from the group consisting of vancomycin, daptomycin, ciprofloxacin, ceftazidime, and ceftibuten. The antibiotic may be released over a period of about 3 weeks.

In a further embodiment, a method of manufacturing an active agent-eluting hemostatic agent is presented comprising: preparing a solution of gelatin; isolating a carboxyl group concentration from the gelatin solution; incubating at least one active agent, having at least one amine or carboxylate group in its structure, and a crosslinking agent with the isolated carboxyl group concentration for between about 1 hour to about 24 hours to form a product; and precipitating the product to form the active agent-eluting hemostatic agent. The gelatin may be crosslinked by a chemical crosslinker selected from the group consisting of 1-ethyl-3-(3-dimethylaminopropyl) carbodiimide (EDC) and dicyclohexylcarbodiimide (DCC), and carbonyldiimidazole (CDI). In some embodiments, the crosslinking agent is EDC.

The at least one active agent may be an anesthetic, an antimicrobial or a combination thereof. In embodiments in which the at least one active agent is an antimicrobial, the antimicrobial may be an antibiotic that may be selected from a group consisting of glycopeptide antibiotics, lipopeptide antibiotics, quinolones, and cephalosporins. Specifically, the antibiotic may be selected from the group consisting of vancomycin, daptomycin, ciprofloxacin, ceftazidime, and ceftibuten.

In alternate embodiments, the at least one active agent may be an anesthetic such as a non-steroidal anti-inflammatory drug (NSAID). The NSAID may be selected from the group consisting of aspirin, ibuprofen, naproxen and naproxen sodium, diclofenac, oxaprozin, etodolac, indomethacin, ketolorac, and vimovo.

BRIEF DESCRIPTION OF THE DRAWINGS

For a fuller understanding of the invention, reference should be made to the following detailed description, taken in connection with the accompanying drawings, in which:

FIG. 1A-B are a series of images depicting schematics of gelatin conjugation with vancomycin and daptomycin. Gelatin structure is simplified to show representative carboxylates or amines that may form peptide bonds with the antibiotic of interest when conjugated in the presence of EDC. (A) Carboxylates (shown in grey) on the antibiotics that may form a peptide bond with amine groups in gelatin. (B) Amines (shown in grey) on the antibiotics that may form a peptide bond with carboxylate groups in gelatin.

FIG. 2A-D are a series of images depicting SEM micrographs of antibiotic-releasing hemostatic agents. (A & B) Vancomycin hemostatic agents at 270× and 450× magnifications, respectively. (C & D) Daptomycin hemostatic agents at 270× and 500× magnifications, respectively.

FIG. 4A-D are a series of graphs depicting in vitro release of antibiotic from antibiotic-eluting hemostatic agents. Each preparation was loaded with indicated antibiotic concentrations. (A & C) Cumulative release (mg) of vancomycin and daptomycin, respectively. (B & D) Cumulative release (%) of total antibiotic loaded in the hemostatic agent for vancomycin and daptomycin, respectively.

FIG. 5A-B is a series of images depicting FTIR spectra of antibiotic released from hemostatic agents. Pure vancomycin or daptomycin standards were compared to samples released from hemostatic agents. Pure vancomycin (A) or daptomycin (B); both in dark grey as compared to samples released from the hemostatic agents after 2 weeks; both in light grey.

FIG. 6A-C are a series of images depicting bacterial inhibition by vancomycin released from hemostatic agents. (A) Cultured *S. aureus* was subjected to vancomycin released from either 48 h samples or 2-week samples of antibiotic-eluting hemostatic agent. Dilution 1 contains 9.875 g/mL for 48 h or 18.25 g/mL vancomycin in the 2-week samples. Subsequent dilutions reflect a 50% reduction in concentration of the previous dilution. (B) Agar coated with *S. aureus* exposed to vancomycin-eluting hemostatic agent (1), crosslinked gelatin (2), untreated control disk (3), and 50 g vancomycin control disk (4). (C) Agar coated with *S. aureus* exposed to daptomycin-eluting hemostatic agent (1), crosslinked gelatin (2), untreated control disk (3), and 50 g daptomycin control disk (4).

FIG. 7A-B are a series of graphs depicting normalized cell viability for fibroblasts treated with antibiotic-eluting hemostatic agents. (A) Viability of cells in response to vancomycin-eluting hemostatic agent samples from 48-hour release and controls including equivalent concentration of vancomycin and crosslinked gelatin. (B) Viability of cells in response to daptomycin-eluting hemostatic agent and controls.

FIG. 16A-B are a series of graphs depicting in vitro release of diclofenac from diclofenac-eluting hemostatic agents. Each preparation was loaded with indicated concentrations. (A) Cumulative release (mg) of diclofenac. (B) Cumulative release (%) of total diclofenac loaded in the hemostatic agent.

DETAILED DESCRIPTION OF THE PREFERRED EMBODIMENT

Figure 3:
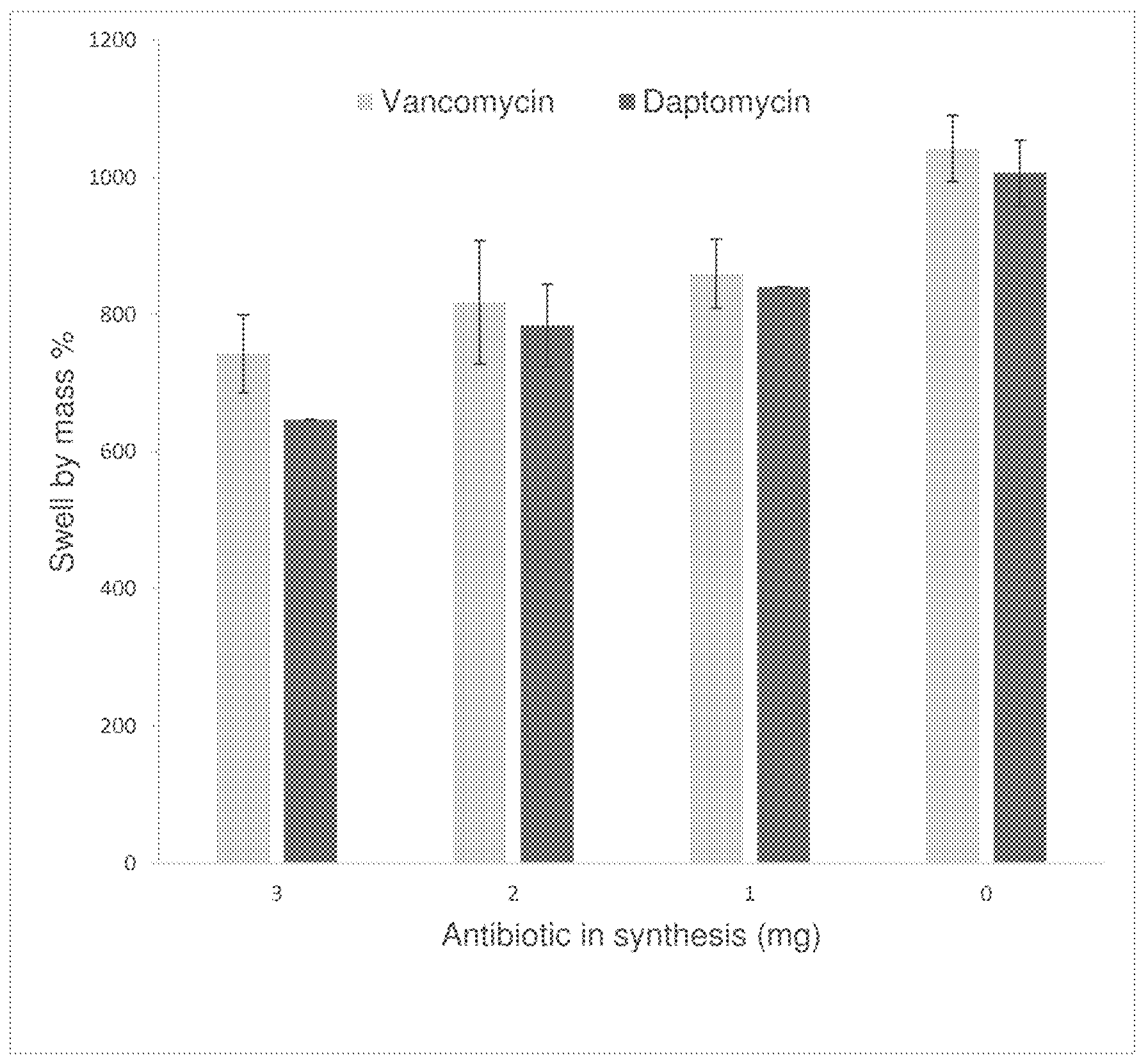
FIG. 3 is a graph depicting the swelling degree of antibiotic-eluting hemostatic agents. Each preparation was loaded with indicated antibiotic concentrations and allowed to swell for 24 hours. 0 mg of antibiotic used buffer in place of antibiotic for total volume and are reflective of crosslinked gelatin only.

In the following detailed description of the preferred embodiments, reference is made to the accompanying drawings, which form a part hereof, and within which are shown by way of illustration specific embodiments by which the invention may be practiced. It is to be understood that other embodiments may be utilized, and structural changes may be made without departing from the scope of the invention.

Definitions

All numerical designations, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

The term "about" or "approximately" as used herein refers to being within an acceptable error range for the particular value as determined by one of ordinary skill in the art, which will depend in part on how the value is measured or determined. As used herein, the term "about" refers to ±10%.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

As used in the specification and claims, the singular form "a", "an" and "the" include plural references unless the context clearly dictates otherwise. For example, the term "a nanoparticle" includes a plurality of nanoparticles, including mixtures thereof.

As used herein, the term "comprising" is intended to mean that the products, compositions, and methods include the referenced components or steps, but not excluding others. "Consisting essentially of" when used to define products, compositions, and methods, shall mean excluding other components or steps of any essential significance. "Consisting of" shall mean excluding more than trace elements of other components or steps.

"Patient" is used to describe an animal, preferably a human, to whom treatment is administered, including prophylactic treatment with the compositions of the present invention.

"Pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pennsylvania, Mack Publishing Company, $19^{th}$ ed.) describes formulations which can be used in connection with the subject invention.

The terms "administer" or "administering" as used herein are defined as the process by which the compositions of the present invention are delivered to the patient for treatment or prevention purposes. The composition can be delivered topically in dosage unit formulations containing conventional nontoxic pharmaceutically acceptable carriers, adjuvants, and vehicles as desired. The compositions can be administered prior to or after wound closure. Administration may occur once or multiple times.

"Sustained release" as used herein refers to a composition comprising a therapeutically effective amount of the active agent-eluting hemostatic agent, when administered to a patient, continuously releases a stream of one or more active agents over a predetermined time period at a level sufficient to achieve a desired effect, such as preventing or treating infections, inflammation or pain, throughout the predetermined time period. Reference to a continuous release stream is intended to encompass release that occurs as the result of biodegradation of the composition, or component thereof, or as the result of metabolic transformation or dissolution of the added nutrients or other desired agents.

"Active agent" as used herein is defined as a substance, component or agent that has measurable specified or selective physiological activity when administered to an individual in a therapeutically effective amount. Examples of active agents as used in the present invention include anesthetics and antimicrobials such as antibiotics, antivirals, antifungals, antiprotozoals, and antiparasitics. At least one active agent is used in the compositions of the present invention. The active agent should have at least one amine or carboxylate group in its structure to ensure binding with the hemostatic agent.

A "therapeutically effective amount" as used herein is defined as concentrations or amounts of components which are sufficient to effect beneficial or desired clinical results, including, but not limited to, any one or more of treating symptoms of infection, inflammation or pain and preventing infection or treating or preventing pain, inflammation or infection.

"Prevention" or "preventing" as used herein refers to any of: halting the effects of infection or pain, reducing the effects of infection or pain, reducing the incidence of infection or pain, reducing the development of infection or pain, delaying the onset of symptoms of infection or pain, increasing the time to onset of symptoms of infection or pain, and reducing the risk of development of infection or pain.

"Treatment" or "treating" as used herein refers to any of the alleviation, amelioration, elimination and/or stabilization of a symptom, as well as delay in progression of a symptom of a particular disorder. For example, "treatment" may include any one or more of the following: amelioration and/or elimination of one or more symptoms associated with infection, inflammation, or pain; reduction of one or more symptoms of infection, inflammation, or pain; stabilization of symptoms of infection, inflammation, or pain; and delay in progression of one or more symptoms of infection, inflammation, or pain.

"Infection" as used herein refers to the invasion of one or more microorganisms such as bacteria, viruses, fungi, yeast, or parasites in the body of a patient in which they are not normally present.

"Antibiotics" as used herein refers to natural or synthetic compositions capable of killing or inhibiting growth of bacteria. Exemplary antibiotics that may be used herein include any antibiotic having at least one amine or carboxylate group in its structure including, but not limited to, glycopeptide antibiotics, lipopeptide antibiotics, cephalosporins, and quinolones. Examples of glycopeptide antibiotics include, but are not limited to, vancomycin, teicoplanin, oritavancin, telavancin, and dalbavancin. In some embodiments in which vancomycin is used, the concentration can be between about 0.069 mM to about 2.07 mM, including all amounts in between. Examples of lipopeptide antibiotics include, but are not limited to, daptomycin, surfactin, iturin, fengycin, and polymyxin. In some embodiments in which daptomycin is used, the concentration can be between about 0.8 mM to about 1.85 mM, including all amounts in between. Examples of cephalosporins include, but are not limited to, ceftazidime, ceftibuten, cefazolin, cefaclor, cefdinir, cefuroxime, cefadroxil, cephalexin, cefepime, ceftriaxone, cefotetan, cefoxitin, cefprozil, ceftaxime, cefditoren, cefixime, cefpodoxime, ceftaroline, Cefacetrile (cephacetrile), Cefadroxil (cefadroxyl; Duricef®), Cefalexin (cephalexin; Keflex®), Cefaloglycin (cephaloglycin), Cefalonium (cephalonium), Cefaloridine (cephaloradine), Cefalotin (cephalothin; Keflin®), Cefapirin (cephapirin; Cefadryl®), Cefatrizine, Cefazaflur, Cefazedone, Cefazolin (cephazolin; Ancef®, Kefzol®), Cefradine (cephradine; Velosef®), Cefroxadine, Ceftezole, Cefaclor (Ceclor®, Distaclor®, Keflor®, Raniclor®), Cefonicid (Monocid®), Cefprozil (cefproxil; Cefzil®), Cefuroxime (Altacef®, Zefu®, Zinnat®, Zinacef®, Ceftino, Biofuroksym®, Xorimax®), Cefuzonam, Cefaloram, Cefmetazole, Cefotetan, Cefoxitin, Loracarbef, Cefbuperazone, Cefmetazole (Zefazone®), Cefminox, Cefotetan (Cefotan®), Cefoxitin (Mefoxin®), Cefotiam (Pansporin®), Cefcapene, Cefdaloxime, Cefdinir (Sefdin®, Zinir®, Omnicef®, Kefnir®), Cefditoren, Cefetamet, Cefixime (Fixx®, Zifi®, Suprax®), Cefmenoxime, Cefodizime, Cefotaxime (Claforan®), Cefovecin (Convenia®), Cefpimizole, Cefpodoxime (Vantin®, PECEF®, Simplicef®), Cefteram, Ceftibuten (Cedax®), Ceftiofur (Naxcel®, Excenel®), Ceftiolene, Ceftizoxime (Cefizox®), Ceftriaxone (Rocephin®), Cefoperazone (Cefobid®), Ceftazidime (Meezat®, Fortum®, Fortaz®), Latamoxef (moxalactam), Cefclidine, Cefepime (Maxipime®), Cefiderocol (Fetroja®), Ceflupenam, Cefoselis, Cefozopran, Cefpirome (Cefrom®), Flomoxef, Ceftobiprole, Ceftaroline, Ceftolozane, Cefaparole, Cefcanel, Cefedrolor, Cefempidone, Cefetrizole, Cefivitril, Cefmatilen, Cefmepidium, Cefoxazole, Cefrotil, Cefsumide, Ceftioxide, Cefuracetime, and Nitrocefin. Exemplary quinolones include, but are not limited to, fluoroquinolones such as ciprofloxacin, levofloxacin, gemifloxacin, and moxifloxacin.

"Antimicrobial" as used herein refers to natural or synthetic compositions capable of killing or inhibiting the growth of microorganisms including, but not limited to, bacteria, fungi, viruses, protozoa, and parasites. Antimicrobials that may be used include those having at least one amine or carboxylate group in its structure. Antimicrobials used herein include antibiotics, antivirals, antifungals, antiprotozoals, and antiparasitics. Exemplary antimicrobials that may be used herein include, but are not limited to, the antibiotics as defined previously, povidone-iodine, iodine, and betadine.

"Anesthetics" as used herein refers to a natural or synthetic composition capable of producing a local, regional, or general loss of sensation. Anesthetics are generally used to induce an insensitivity to pain. The terms "anesthetic" and "analgesic" are used interchangeably herein. Anesthetics that may be used include those having at least one amine or carboxylate group in its structure. As used herein, the term "anesthetic" may refer to local anesthetics. Exemplary local anesthetics that may be used herein include, but are not limited to, lidocaine, marcaine, bupivacaine, prilocaine, mepivacaine, etidocaine, ropivacaine, and levobupivacaine. "Anesthetic" may also refer to compositions exhibiting anti-inflammatory properties such as non-steroidal anti-inflammatory drugs (NSAIDs). Exemplary NSAIDs useful herein include, but are not limited to, aspirin, ibuprofen, naproxen and naproxen sodium, diclofenac, oxaprozin, etodolac, indomethacin, ketolorac, and vimovo.

"Hemostatic agent" as used herein refers to a substance or composition used to stop bleeding, hemorrhage, or blood flow through a vessel or body part. In some embodiments, the hemostatic agent may be a polymer matrix forming a physical barrier over the surgical site or wound. In some embodiments, the hemostatic agent has a paste-like consistency. Examples of hemostatic agents include, but are not limited to, gelatin, collagen, chitosan, and derivatives thereof. In a preferred embodiment, crosslinked gelatin is used as the hemostatic agent. The hemostatic agent preferably has a semisolid paste-like consistency that is more solid than a hydrogel but less solid than a sponge. In other embodiments, the hemostatic agent has the consistency of a dry powder which may be clumpy. In other embodiments, a pharmaceutically active carrier is added to the dry powder to achieve a paste-like consistency. The term "conjugate" is used synonymously herein with "hemostatic agent".

"Polymer" as used herein refers to a relatively high molecular weight organic compound, natural or synthetic, whose structure can be represented by a repeated small unit, the monomer. Synthetic polymers are typically formed by addition or condensation polymerization of monomers. Examples of polymers that can be used as hemostatic agents include, but are not limited to, gelatin, collagen, and derivatives thereof.

"Crosslinking" as used herein refers to chemically joining two or more molecules by a covalent bond. As used herein, crosslinking the hemostatic agent, such as gelatin, with a chemical crosslinking agent forms cages in the hemostatic agent. Crosslinking also allows one of more anesthetics or antimicrobials to be covalently bound directly to the gelatin and to be encapsulated in the cages formed in the gelatin. Exemplary crosslinking agents include, but are not limited to, carbodiimides such as 1-ethyl-3-(3-dimethylaminopropyl) carbodiimide (EDC) and dicyclohexylcarbodiimide (DCC); carbonyldiimidazole (CDI). Controlling crosslink density is of vital importance. Too much crosslinking results in a sponge, which is not desirable. While crosslinking at lower concentrations does not allow the cages to form, thus releasing the antibiotic too quickly. Concentrations of the crosslinking agent and the hemostatic agent, such as gelatin, are controlled to ensure steady elution profiles of the antibiotic. In some embodiments in which EDC is used as the crosslinking agent, the concentration can be between about 20 mM to about 50 mM, including all amounts in between.

"Gelatin" as used herein refers to a water-soluble polymer obtained from acid, alkaline or enzymatic hydrolysis of collagen. Gelatin derived from acid treatment is referred to as type A while gelatin derived from alkaline treatment is referred to as type B. In some embodiments, the gelatin may be derived from porcine skin, bovine skin, bone, poultry, or fish. In other embodiments, the gelatin may be a recombinant gelatin. In some embodiments, the gelatin used is Type B gelatin. In some embodiments, the amount of gelatin used may be between about 5 mg/mg to about 20 mg/ml, including all amount in between.

"Paste-like" as used herein refers to a semisolid composition capable of being spread over a wound site and is thicker than a hydrogel but not solid like a sponge.

"Hydrogel" as used herein refers to a three-dimensional network of hydrophilic polymers capable of swelling in water and holding a large amount of water while maintaining the structure due to physical or chemical crosslinking of individual polymer chains. Hydrogels have an elastic, jelly-like structure.

"Sponge" as used herein refers to a solid, water-insoluble, non-elastic, pliable biocompatible material capable of being used in the body as a hemostatic agent.

The inventors have developed glycopeptide and lipopeptide-eluting hemostatic agents that are suitable in the prevention of SSIs. These antibiotic-eluting hemostatic agents are novel in their approach to long-term release of antibiotics within surgical sites through the use of EDC for gelatin crosslinking in addition to specific conjugation of the antibiotic to the gelatin, yielding a continuous release of antibiotic greater than the minimum inhibitory concentrations (MIC) but lower than toxicity levels. (Kshetry, A. O.; Pant, N. D.; Bhandari, R.; Khatri, S.; Shrestha, K. L.; Upadhaya, S. K.; Poudel, A.; Lekhak, B.; Raghubanshi, B. R., Minimum inhibitory concentration of vancomycin to methicillin resistant *Staphylococcus aureus* isolated from different clinical samples at a tertiary care hospital in Nepal. *Antimicrobial Resistance & Infection Control* 2016, 5 (1), 27; Van Hal, S.; Lodise, T. P.; Paterson, D. L., The clinical significance of vancomycin minimum inhibitory concentration in *Staphylococcus aureus* infections: a systematic review and meta-analysis. *Clinical Infectious Diseases* 2012, 54 (6), 755-771; Strom, R. G.; Pacione, D.; Kalhorn, S. P.; Frempong-Boadu, A. K., Decreased risk of wound infection after posterior cervical fusion with routine local application of vancomycin powder. *Spine* (Phila Pa 1976) 2013, 38 (12), 991-4; Wukich, D. K.; Dikis, J. W.; Monaco, S. J.; Strannigan, K.; Suder, N. C.; Rosario, B. L., Topically Applied Vancomycin Powder Reduces the Rate of Surgical Site Infection in Diabetic Patients Undergoing Foot and Ankle Surgery. *Foot Ankle Int* 2015, 36 (9), 1017-24; Charlton, C. L., Hindler, J. A., Turnidge, J., & Humphries, R. M. Precision of vancomycin and daptomycin MICs for methicillin-resistant *Staphylococcus aureus* and effect of subculture and storage. Journal Clin Micro. 2014, 52(11), 3898-3905).

The combination of commonly utilized surgical aids, gelatin as a hemostatic agent, and vancomycin as a highly effective antibiotic against MRSA, yields an efficient and safe method for delivering both to aid in the prevention of SSIs.

The following non-limiting examples illustrate exemplary systems and components thereof in accordance with various embodiments of the disclosure. The examples are merely illustrative and are not intended to limit the disclosure in any way. While the examples are drawn to antibiotics and NSAIDs, other agents are contemplated as being useful for incorporation in the hemostatic agent of the invention described herein.

Example 1—Vancomycin and Daptomycin

The antibiotic-eluting hemostatic agent described herein provides for the continuous release of antibiotics for a minimum of 3 weeks, which exceeds the release previously shown for vancomycin. (Shukla, A.; Fang, J. C.; Puranam, S.; Hammond, P. T., Release of vancomycin from multilayer coated absorbent gelatin sponges. *J Control Release* 2012, 157 (1), 64-71; Zhou, J.; Fang, T.; Wang, Y.; Dong, J., The controlled release of vancomycin in gelatin/0-TCP composite scaffolds. *Journal of biomedical materials research Part A* 2012, 100 (9), 2295-2301; Shukla, A.; Avadhany, S. N.; Fang, J. C.; Hammond, P. T., Tunable Vancomycin Releasing Surfaces for Biomedical Applications. Small 2010, 6 (21), 2392-04).

Figure 1A:
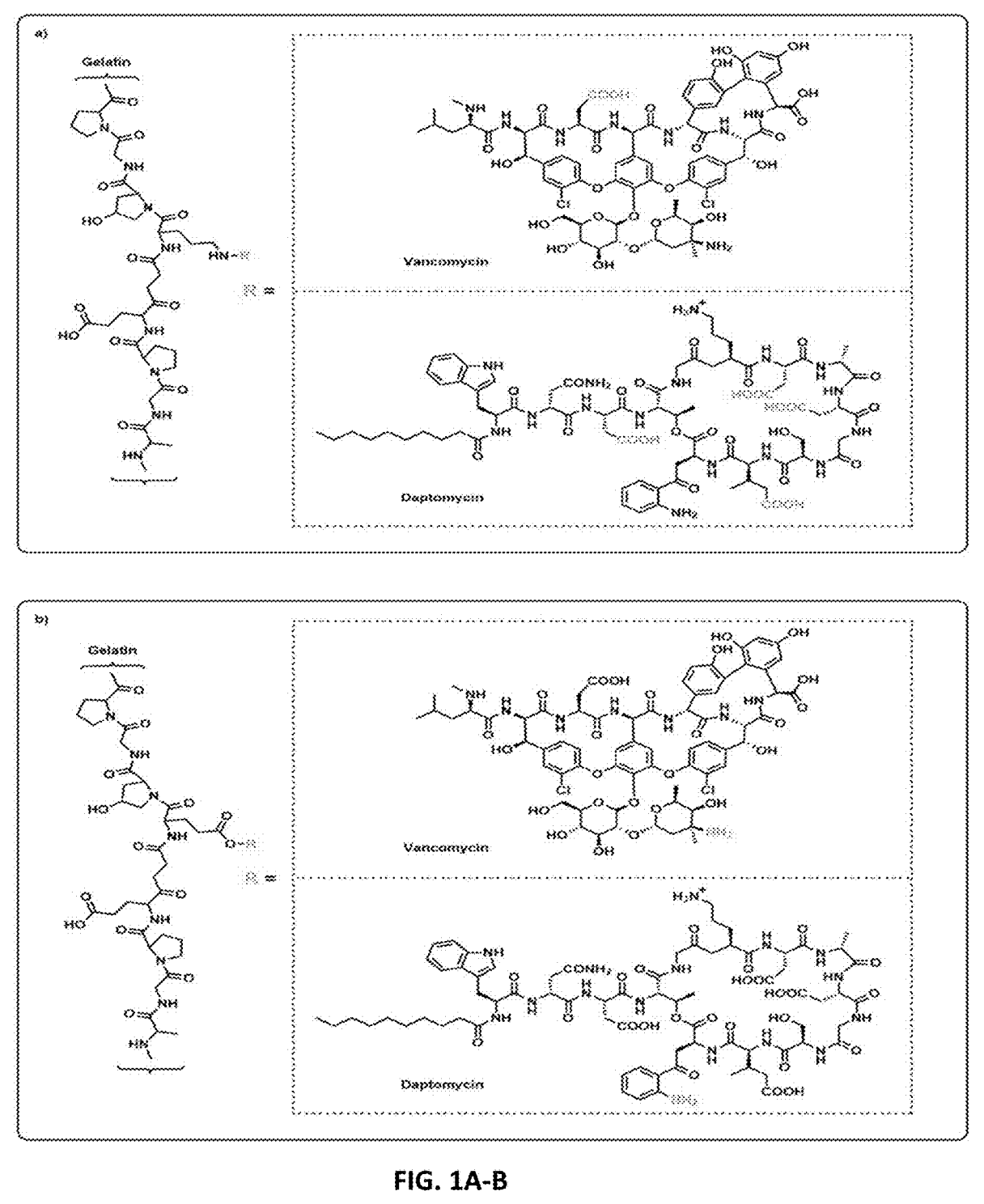

This functionality is accomplished through the use of carbodiimide chemistry to create crosslinked gelatin cages to entrap the antibiotic for immediate release while allowing for direct antibiotic conjugation with gelatin, providing a delayed release. As shown in FIG. 1, the degree of crosslinking between the gelatin and the antibiotic is associated with the availability of carboxyl and amino functional groups on the antibiotic. Hence, more available groups lead to additional conjugation (formation of amide bonds) between the gelatin and antibiotic. Increased rates of amide bond formation between the antibiotic and gelatin lead to slower release as depicted within the comparison of vancomycin and daptomycin shown in FIG. 4, as daptomycin has three additional carboxylates that can be used for conjugation.

Analysis to determine concentrations of antibiotic released from the hemostatic agent via HPLC revealed that the structure of the released antibiotic differed slightly in later release samples. Retention times of the samples following the 24-hour release were slightly longer than those of the standards. This was likely due to dimerization or trimerization of the antibiotic, antibiotic conjugation to short amino acid sequences derived from gelatin, or a combination of the two. Microdilution and modified Kirby-Bauer assays shown in FIG. 6 reveal that vancomycin released from the hemostatic agent maintains its ability to inhibit the growth of *S. aureus* after a 2-week period. Taken together, these experiments indicate that even though the structure of the antibiotic may have changed slightly in later release samples, the potentially modified, released vancomycin maintains efficacy.

The antibiotic-eluting hemostatic agents developed here incorporate a crosslinked gelatin with an antibiotic. In some embodiments the crosslinker can be EDC. Although EDC itself is highly toxic, it has been shown to be minimally toxic following complete reactivity with its preferred functional groups. (Zhou, J.; Fang, T.; Wang, Y.; Dong, J., The controlled release of vancomycin in gelatin/β-TCP composite scaffolds. *Journal of biomedical materials research Part A* 2012, 100 (9), 2295-2301; Cammarata, C. R.; Hughes, M. E.; Ofner, C. M., 3rd, Carbodiimide induced crosslinking, ligand addition, and degradation in gelatin. *Mol Pharm* 2015, 12 (3), 783-93). The method in the current study utilized differences in solubility to minimize free or unreacted EDC in the final product, thereby ensuring that the antibiotic-eluting hemostatic agent is biocompatible as shown in FIG. 7. Additionally, studies in which gelatin was complexed with beta-TCP via various concentrations of EDC, showed that minimal concentrations of EDC (up to 10 mg/mL) were negligibly cytotoxic to cultured cells. (Zhou, J.; Fang, T.; Wang, Y.; Dong, J., The controlled release of vancomycin in gelatin/β-TCP composite scaffolds. *Journal of biomedical materials research Part A* 2012, 100 (9), 2295-2301).

Materials and Methods

Materials

Gelatin type B, 2-(N-morpholino)ethanesulfonic acid (MES), vancomycin, daptomycin, ceftazidime, 1-ethyl-3-(3-dimethylaminopropyl) carbodiimide (EDC), and absolute ethanol were purchased from Fischer Scientific (Waltham, MA). Ceftibuten and NaCl were purchased from Sigma-Aldrich (St. Louis, MO). Tryptic soy agar and broth were purchased Difco Laboratories (Sparks, MD). HEK-293 fibroblasts and *Staphylococcus aureus* 25923 were obtained from ATCC (Manassas, VA).

Preparation of Antibiotic-Eluting Hemostatic Agents

Gelatin was prepared as a 20 mg/mL stock solution in 0.05 M MES buffer pH 5.0 with stirring at 50° C. until soluble. To prepare the hemostatic agents, 20 mM carboxyl group concentration from the gelatin stock was incubated with either vancomycin (2.07 mM), or daptomycin (1.85 mM), under activation by EDC (60 mM) for 2 hours at 50 rpm and 22° C. The product was precipitated under ice-cold absolute ethanol followed by centrifugation at 6000×g, then dissolved in 1.85 mM NaCl for washing, followed by a second round of precipitation. Hemostatic agents were vacuum dried and heated at 80° C. to remove residual ethanol. The hemostatic agents are in a clumpy powder form after heating. The hemostatic agents may be administered in powder form or alternatively, an amount of phosphate buffered saline (PBS) may be added to achieve a paste-like consistency.

Varying the concentration of crosslinking agent and the reaction time highly impact the structure of the hemostatic agent. In some embodiments, the concentration of EDC is between about 20 mM and about 60 mM. Reaction time can be between about 1 hour to about 24 hours. In some embodiments, 0.1 M NaHCO may be used in place of 0.05 M MES buffer.

Structural Analysis of Hemostatic Agents

Hemostatic agent morphology was examined by scanning electron microscopy (SEM) using a JEOL JSM-6490 microscope. Hemostatic agents were fixed in 10% formaldehyde for 2 hours, dehydrated with ethanol, and selected for mounting on double-sided conductive carbon tape.

Antibiotic Release from Antibiotic-Eluting Hemostatic Agents

For release profile determination, hemostatic agents were combined with 0.5 mL phosphate-buffered saline solution (PBS) to make a semisolid followed by immersion in 1 mL PBS. Samples were incubated at 37° C. and 100% relative humidity over a period of 3 weeks with 1 mL of PBS removed and then replaced with fresh PBS at 24, 48, 72, 96, 168, 336, and 504 hours. Release samples were stored at −80° C. until analysis to determine drug release kinetics of the hemostatic agents. Release samples were filtered through syringe filters (0.45 m) and were analyzed by high performance liquid chromatography (Waters HPLC, 1100 series) to determine antibiotic concentrations. Samples were run for 10 min using 70/30 PBS/methanol mobile phase, 1 mL/min flow rate with a 150 L injection volume on a C18 reverse phase column (Supelco) coupled with UV detection (280 nm for vancomycin or 223 nm for daptomycin). Peak height was correlated with standards of known concentrations of the perspective antibiotic used in the hemostatic agent to determine antibiotic concentration in the released samples.

Fourier Transform Infrared Spectroscopy

FTIR spectra were collected on a Nicolet Is10 to ensure structural integrity of antibiotics released from the hemostatic agents. Released samples were scanned in the range between 4000 and 800 $cm^{-1}$.

Bacterial Growth Inhibition and Efficacy of Released Antibiotic

Inhibition of S. *Aureus* 25293 or *E. Coli* (Migula) Castellani and Chalmers by antibiotic-eluting hemostatic agents was determined through modified Kirby-Bauer disk diffusion tests and microdilution assays. Throughout all Kirby-Bauer tests, agar plates were formed using tryptic soy agar. The plates were subsequently coated with the appropriate strain within its exponential growth phase at a concentration of $10^8$ CFU/mL. Filter papers that had been incubated with the hemostatic agents, gelatin, or pure antibiotic equivalent to 24-hour release concentrations for two hours were then immediately placed upon the plates. Zones of inhibition were measured and photographed following 16-18 hours of incubation at 37° C. Microdilution assays were performed in triplicate using the appropriate bacteria in 96-well plates and done in serial two-fold dilutions. Bacteria grown to its exponential growth phase diluted in tryptic soy broth to $10^5$ CFU/mL was used for the assays. Following 16-18-hour incubation at 37° C., optical density at 600 nm for treated and control bacteria was examined via a BioTek PowerWave XS plate reader. The normalized bacterial inhibition was then calculated from Equation (1).

$$\text{Normalized bacteria inhibition} = \frac{(OD600\ \text{positive control} - OD600\ \text{sample})}{(OD600\ \text{positive control} - OD600\ \text{negative control})} \tag{1}$$

Biocompatibility Analysis of Antibiotic-Eluting Hemostatic Agents

Hemostatic agent biocompatibility was established by examining cell viability of HEK-293T fibroblasts upon exposure to hemostatic agent eluent, pure antibiotic, and crosslinked gelatin samples. Cells were maintained in complete media (DMEM supplemented with 10% fetal bovine serum, 1 mM sodium pyruvate, and 1 mM penicillin/streptomycin at 37° C. in 5% $CO_2$). For analysis, cells were seeded at 10,000 cells per well in 96 well polystyrene tissue culture plates and incubated in complete media (100 uL) at 37° C. for 24 hours. Hemostatic agents were allowed to completely elute in culture media at 37° C. for 24 hours. Gelatin (0.3 mg/mL) and pure antibiotics (0.1 mg/mL) were also incubated in culture media for 24 hours. All samples were filtered through 0.2 m filters, and the media on the growing cells was replaced with of test media (100 L). Positive controls were cells cultured in untreated media, while negative controls contained untreated media and no cells. Following 18-hour exposure to the test media, dye solution (15 l) was administered to each well and the plate was incubated at 37° C. for 3 hours in a humidified, 5% $CO_2$ atmosphere. After incubation, solubilization solution/stop mix (100 kl) was added to each well. A BioTek PowerWave XS plate reader was used to detect the absorbance of the wells at 600 nm to elucidate cell viability. Cell viability was calculated from Equation (2).

$$\text{Normalized cell viability} = \frac{(\text{Abs600 sample} - \text{Abs600 negative control})}{(\text{Abs600 positive control} - \text{Abs600 negative control})} \tag{2}$$

Results

Characterization of Antibiotic-Eluting Hemostatic Agents

Gelatin type-B was used for all conjugations as it is known to possess increased concentrations of carboxylate groups in relation to other forms (30). Slightly acidic conditions (pH 5-7) in 0.05 M MES ensured the availability of carboxylate groups for nucleophilic attack by EDC to promote enhanced reactivity in an effort to generate highly crosslinked gelatin. (Kosasih, A. B., B. J.; Wigent, R. J.; & Ofner III, C. M., Characterization and in vitro release of methotrexate from gelatin/methotrexate conjugates formed using different preparation variables. *International Journal of Pharmaceutics* 2000, 204 (1), 81-89). Crosslinking reactions performed in the presence of antibiotics allowed for the trapping of antibiotics in cage-like, crosslinked gelatin structures in addition to the direct conjugation of the antibiotic to the gelatin. Possible binding outcomes of vancomycin or daptomycin with gelatin are illustrated in FIG. 1.

SEM micrographs of the prepared hemostatic agents containing either vancomycin or daptomycin are shown in FIG. 2. Upon examination of the surface features of the hemostatic agents, a compact glassy layered morphology was seen. There were slight differences between the vancomycin and daptomycin-linked hemostatic agents as the vancomycin hemostatic agents demonstrated increased surface variations and "pitting" (FIG. 2B) in comparison to the smoother morphology of the daptomycin hemostatic agents (FIG. 2D). This is likely due to the increased availability of potential binding groups in the structure of daptomycin, which is likely to lead to increased rates of daptomycin-gelatin conjugation and decreased rates of gelatin-gelatin conjugation.

Swelling Capacity of Antibiotic-Eluting Hemostatic Agents

The swelling behavior of a hemostatic agent plays an important role in absorption of body fluids, metabolites, and regulating nutrients. FIG. 3 shows the swelling behavior of the antibiotic-eluting hemostatic agents with varying concentrations of antibiotic used for each. Compared with conjugated gelatin alone, addition of either vancomycin or daptomycin slightly decreased the swelling capacity of the gelatin. Both vancomycin and daptomycin conjugates exhibited slightly decreased swelling with higher concentrations of antibiotic with a more notable decrease with the daptomycin. This difference can likely be attributed to the additional binding sites on daptomycin which may allow for additional bond formation between the daptomycin and gelatin leading to a more rigid complex. While there was a decrease is swelling of the hemostatic agents, each possessed the ability to swell to more than 600% of their original size and as such, can serve as effective hemostats.

Antibiotic Release from Hemostatic Agents

Release profiles of vancomycin or daptomycin-linked hemostatic agents determined by HPLC are shown in FIG. 4. Vancomycin hemostatic agents revealed a large initial burst effect with a release of 10% of the loaded vancomycin within 48 hours as seen in FIG. 4B. Following the initial burst, release of vancomycin was sustained for over a period of 500 hours until separation was no longer practical.

Daptomycin hemostatic agents initially showed a much slower, linear release likely due to increased rates of direct binding to gelatin and less free daptomycin trapped within the crosslinked gelatin (FIGS. 4A and 4C). Akin to the vancomycin hemostatic agents, the daptomycin hemostatic agents released approximately 20% of the total antibiotic near 500 hours and the complex slowly collapsed following that period (FIG. 4D).

Structure and Efficacy of Released Antibiotics from Hemostatic Agents

Conjugation of antibiotics to gelatin via the activity of EDC may cause structural changes to the antibiotic itself. As such, FTIR spectral data was obtained of the released antibiotic samples. Basic chemical stability of vancomycin and daptomycin were confirmed in all released samples as seen in the representative samples depicted in FIG. 5.

To determine the efficacy of vancomycin released from antibiotic-eluting hemostatic agents, microdilution assays were performed. Therapeutic efficiency was established as shown in FIG. 6A through monitoring the normalized density of *S. aureus* cultured within the presence of dilutions of released vancomycin. Efficacy remained consistent between 48-hour and 336-hour samples, further indicating structural integrity of the released vancomycin and its retained ability to sustain inhibition of bacterial growth over the course of the release. Vancomycin released from the hemostatic agent displayed an MIC between 0.5 and 2 g/mL as previously shown in the literature for pure vancomycin. (Kshetry, A. O.; Pant, N. D.; Bhandari, R.; Khatri, S.; Shrestha, K. L.; Upadhaya, S. K.; Poudel, A.; Lekhak, B.; Raghubanshi, B. R., Minimum inhibitory concentration of vancomycin to methicillin resistant *Staphylococcus aureus* isolated from different clinical samples at a tertiary care hospital in Nepal. *Antimicrobial Resistance & Infection Control* 2016, 5 (1), 27; Van Hal, S.; Lodise, T. P.; Paterson, D. L., The clinical significance of vancomycin minimum inhibitory concentration in *Staphylococcus aureus* infections: a systematic review and meta-analysis. *Clinical Infectious Diseases* 2012, 54 (6), 755-771; Strom, R. G.; Pacione, D.; Kalhorn, S. P.; Frempong-Boadu, A. K., Decreased risk of wound infection after posterior cervical fusion with routine local application of vancomycin powder. *Spine* (Phila Pa 1976) 2013, 38 (12), 991-4; Wukich, D. K.; Dikis, J. W.; Monaco, S. J.; Strannigan, K.; Suder, N. C.; Rosario, B. L., Topically Applied Vancomycin Powder Reduces the Rate of Surgical Site Infection in Diabetic Patients Undergoing Foot and Ankle Surgery. *Foot Ankle Int* 2015, 36 (9), 1017-24).

Modified Kirby-Bauer Assays further confirmed the activity of vancomycin released from hemostatic agents as seen in FIG. 6B. Filter paper with dried antibiotic-eluting hemostatic agent, pure vancomycin, crosslinked gelatin, or filter paper only was placed on *S. aureus* coated agar. A clear zone of inhibition (ZOI) surrounds the vancomycin control (FIG. 6B, panel 4) as well as the antibiotic-eluting hemostatic agent (FIG. 6B, panel 1) which indicated that there was inhibition of *S. aureus* growth.

Similarly, modified Kirby-Bauer Assays also further confirmed the activity of daptomycin released from hemostatic agents as seen in FIG. 6C. Filter paper with dried antibiotic-eluting hemostatic agent, pure daptomycin, crosslinked gelatin, or filter paper only was placed on *S. aureus* coated agar. A clear zone of inhibition (ZOI) surrounds the daptomycin control (FIG. 6C, panel 4) as well as the antibiotic-eluting hemostatic agent (FIG. 6C, panel 1) which indicated that there was inhibition of *S. aureus* growth.

Biocompatibility of Antibiotics Released from Hemostatic Agents

While vancomycin and gelatin have both separately been shown to be minimally toxic to mammalian cells, combination of the two components in the presence of EDC has not. (Shukla, A.; Avadhany, S. N.; Fang, J. C.; Hammond, P. T., Tunable Vancomycin Releasing Surfaces for Biomedical Applications. Small 2010, 6 (21), 2392-04; Yang, G.; Xiao, Z.; Long, H.; Ma, K.; Zhang, J.; Ren, X.; Zhang, J., Assessment of the characteristics and biocompatibility of gelatin sponge scaffolds prepared by various crosslinking methods. Sci Rep. 2018, 8 (1), 1616). Therefore, cell viability of human fibroblasts in the presence of the antibiotic-eluting hemostatic agents was assessed. Media incubated with prepared hemostatic agents containing released antibiotic was applied to cultured cells, as well as control concentrations of antibiotic, and media incubated with crosslinked gelatin. As shown in FIG. 7, cell viability of all released samples was comparable to untreated healthy cells illustrating that the antibiotic released from the hemostatic agent is nontoxic to mammalian cells.

Example 2—Cephalosporins and Quinolones

The antibiotic-eluting hemostatic agent described herein provides for the continuous release of antibiotics for a minimum of 3 weeks. As with Example 1, described above, this functionality is accomplished through the use of carbodiimide chemistry to create crosslinked gelatin cages to entrap the antibiotic for immediate release while allowing for direct antibiotic conjugation with gelatin, providing a delayed release.

Figure 8:
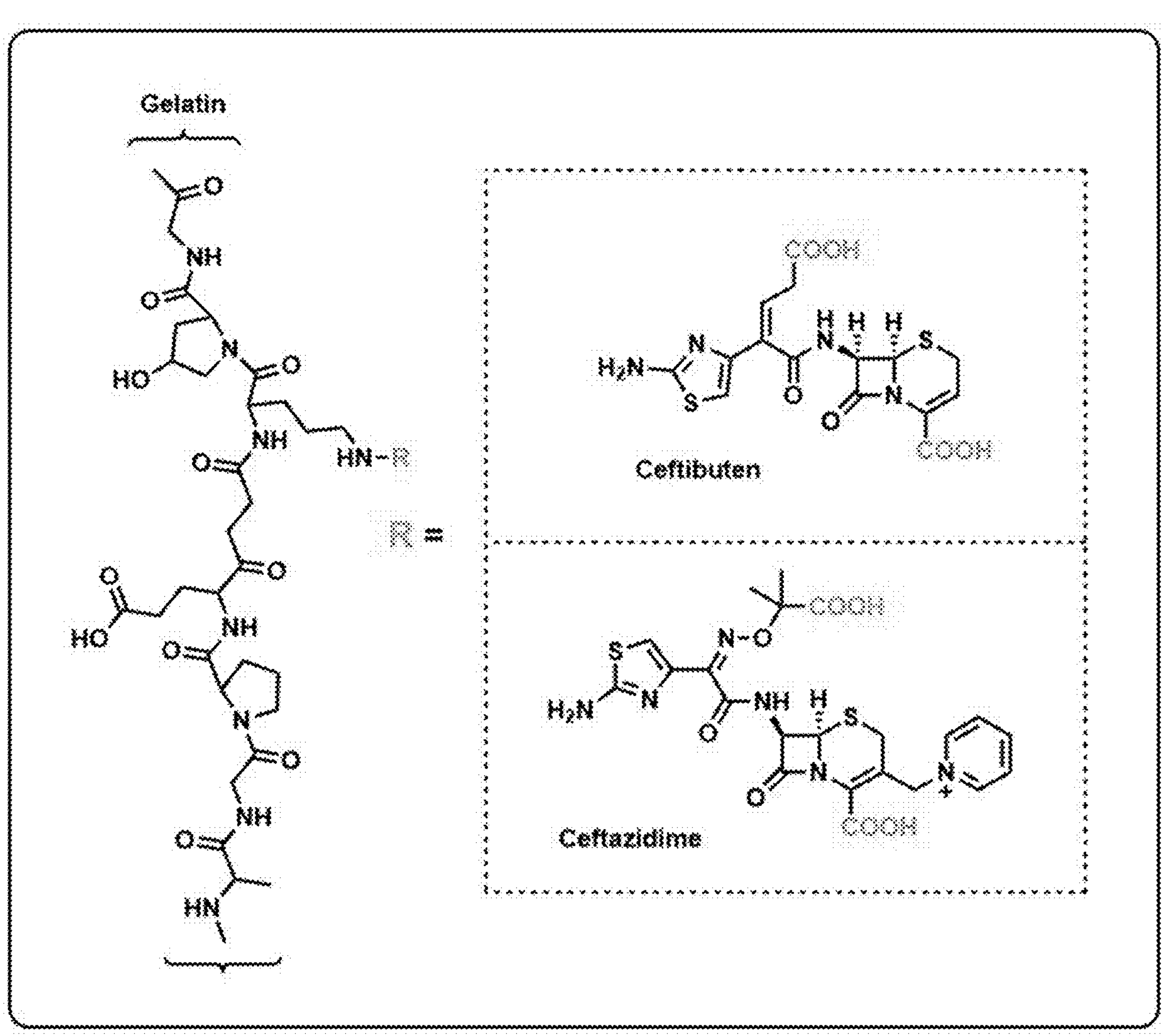
FIG. 8 is an image depicting a schematic of gelatin conjugation with ceftibuten and ceftazidime. Gelatin structure is simplified to show representative amines that may form peptide bonds with the antibiotic of interest when conjugated in the presence of EDC. Carboxylates shown in grey on the antibiotics that may form a peptide bond with amine groups in gelatin.
Figure 9:
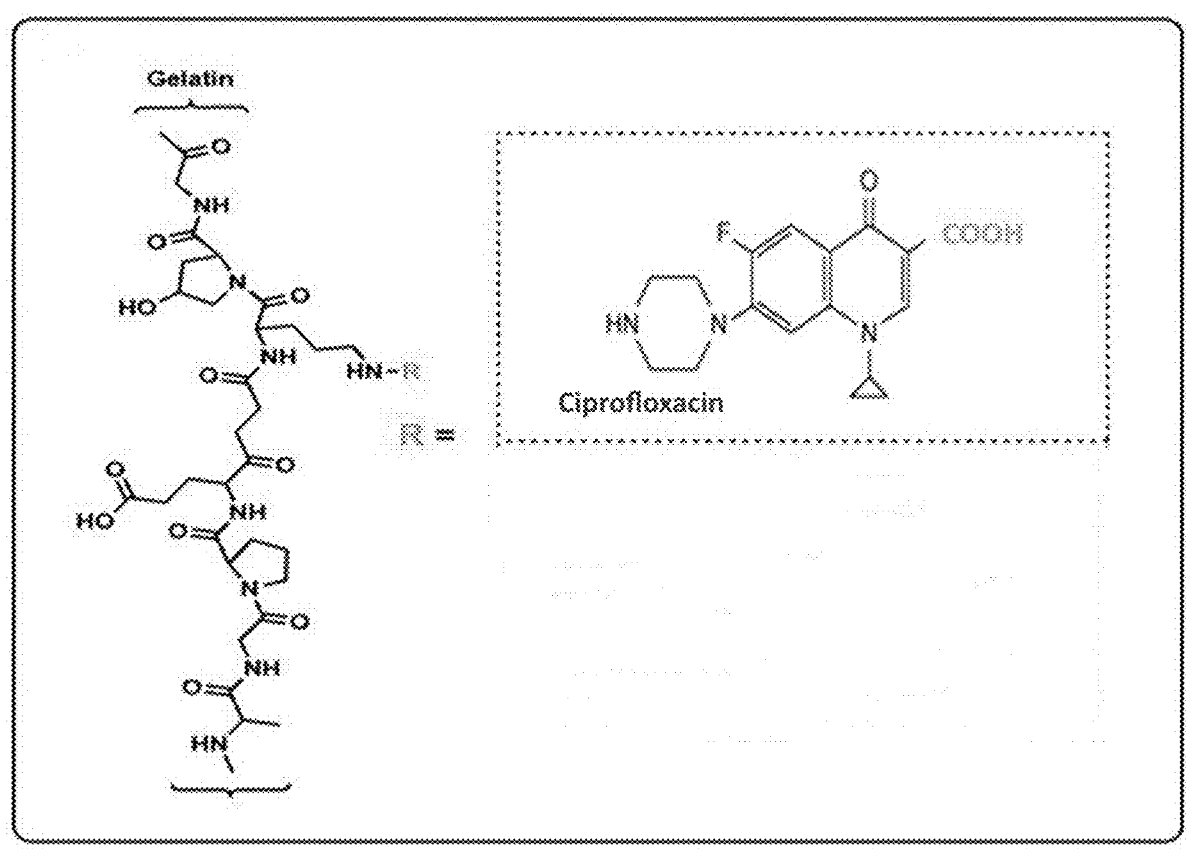
FIG. 9 is an image depicting a schematic of gelatin conjugation with ciprofloxacin. Gelatin structure is simplified to show representative amines that may form peptide bonds with the antibiotic of interest when conjugated in the presence of EDC. Carboxylates shown in grey on the antibiotics that may form a peptide bond with amine groups in gelatin.

As shown in FIGS. 8 and 9, the degree of crosslinking between the gelatin and the antibiotic is associated with the availability of carboxyl and amino functional groups on the antibiotic. Hence, more available groups lead to additional conjugation (formation of amide bonds) between the gelatin and antibiotic. Increased rates of amide bond formation between the antibiotic and gelatin lead to slower release.

Materials and Methods

Materials

Gelatin type B, 2-(N-morpholino)ethanesulfonic acid (MES), ceftazidime, ceftibuten, ciprofloxacin, 1-ethyl-3-(3-dimethylaminopropyl) carbodiimide (EDC), and absolute ethanol were purchased from Fischer Scientific (Waltham, MA). Ceftibuten and NaCl were purchased from Sigma-Aldrich (St. Louis, MO). Tryptic soy agar and broth were purchased Difco Laboratories (Sparks, MD). HEK-293T fibroblasts and *E. Coli* (Migula) Castellani and Chalmers were obtained from ATCC (Manassas, VA).

Preparation of Antibiotic-Eluting Hemostatic Agents

Gelatin was prepared as a 20 mg/mL stock solution in 0.05 M MES buffer pH 5.0 with stirring at 50° C. until soluble. To prepare the hemostatic agents, 20 mM carboxyl group concentration from the gelatin stock was incubated with either ceftibuten (7.31 mM) or ceftazidime (5.49 mM) or ciprofloxacin (0.19 mM) under activation by EDC (60 mM) for 2 hours at 50 rpm and 22° C. The product was precipitated under ice-cold absolute ethanol followed by centrifugation at 6000×g, then dissolved in 1.85 mM NaCl for washing, followed by a second round of precipitation. Hemostatic agents were vacuum dried and heated at 80° C. to remove residual ethanol.

Structural Analysis of Hemostatic Agents

Hemostatic agent morphology was examined by scanning electron microscopy (SEM) using a JEOL JSM-6490 microscope. Hemostatic agents were fixed in 10% formaldehyde for 2 hours, dehydrated with ethanol, and selected for mounting on double-sided conductive carbon tape.

Degree of Swelling of Hemostatic Agents

Samples were prepared as above and complete vacuum dried samples were weighed and measured then immersed in PBS at 37° C. in a humidity-controlled chamber for 24 hours. The sample was removed, blot-dried with an absorbent paper to remove the excess solution and weighed. Swelling capacity was calculated by subtracting the initial mass of the sample from the final mass of the sample after 24 hours as a percentage increase.

Antibiotic Release from Antibiotic-Eluting Hemostatic Agents

For release profile determination, hemostatic agents were combined with 0.5 mL phosphate-buffered saline solution (PBS) to make a semisolid followed by immersion in 1 mL PBS. Samples were incubated at 37° C. and 100% relative humidity over a period of 3 weeks with 1 mL of PBS removed and then replaced with fresh PBS at 24, 48, 72, 96, 168, 336, and 504 hours. Release samples were stored at −80° C. until analysis to determine drug release kinetics of the hemostatic agents. Release samples were filtered through syringe filters (0.45 m) and were analyzed by high performance liquid chromatography (Waters HPLC, 1100 series) to determine antibiotic concentrations. Samples were run for 10 min using 70/30 PBS/methanol mobile phase, 1 mL/min flow rate with a 150 L injection volume on a C18 reverse phase column (Supelco) coupled with UV detection (254 for ceftazidime, 228 for ceftibuten, or 277 for ciprofloxacin). Peak height was correlated with standards of known concentrations of the perspective antibiotic used in the hemostatic agent to determine antibiotic concentration in the released samples.

Fourier Transform Infrared Spectroscopy

FTIR spectra were collected on a Nicolet Is10 to ensure structural integrity of antibiotics released from the hemostatic agents. Released samples were scanned in the range between 4000 and 800 $cm^{-1}$.

Biocompatibility Analysis of Antibiotic-Eluting Hemostatic Agents

Hemostatic agent biocompatibility was established by examining cell viability of HEK-293T fibroblasts upon exposure to hemostatic agent eluent, pure antibiotic, and crosslinked gelatin samples. Cells were maintained in complete media (DMEM supplemented with 10% fetal bovine serum, 1 mM sodium pyruvate, and 1 mM penicillin/streptomycin at 37° C. in 5% $CO_2$). For analysis, cells were seeded at 10,000 cells per well in 96 well polystyrene tissue culture plates and incubated in complete media (100 uL) at 37° C. for 24 hours. Hemostatic agents were allowed to completely elute in culture media at 37° C. for 24 hours. Gelatin (0.3 mg/mL) and pure antibiotics (0.1 mg/mL) were also incubated in culture media for 24 hours. All samples were filtered through 0.2 m filters, and the media on the growing cells was replaced with of test media (100 L). Positive controls were cells cultured in untreated media, while negative controls contained untreated media and no cells. Following 18-hour exposure to the test media, dye solution (15 μl) was administered to each well and the plate was incubated at 37° C. for 3 hours in a humidified, 5% $CO_2$ atmosphere. After incubation, solubilization solution/stop mix (100 l) was added to each well. A BioTek PowerWave XS plate reader was used to detect the absorbance of the wells at 600 nm to elucidate cell viability. Cell viability was calculated from Equation (2).

$$\text{Normalized cell viability} = \frac{(\text{Abs600 sample} - \text{Abs600 negative control})}{(\text{Abs600 positive control} - \text{Abs600 negative control})} \quad (2)$$

Results

Characterization of Antibiotic-Eluting Hemostatic Agents

Crosslinking reactions performed in the presence of antibiotics allowed for the trapping of antibiotics in cage-like, crosslinked gelatin structures in addition to the direct conjugation of the antibiotic to the gelatin. Possible binding outcomes of ceftazidime or ceftibuten with gelatin are illustrated in FIG. 8. Possible binding outcome of ciprofloxacin is shown in FIG. 9.

Figure 10:
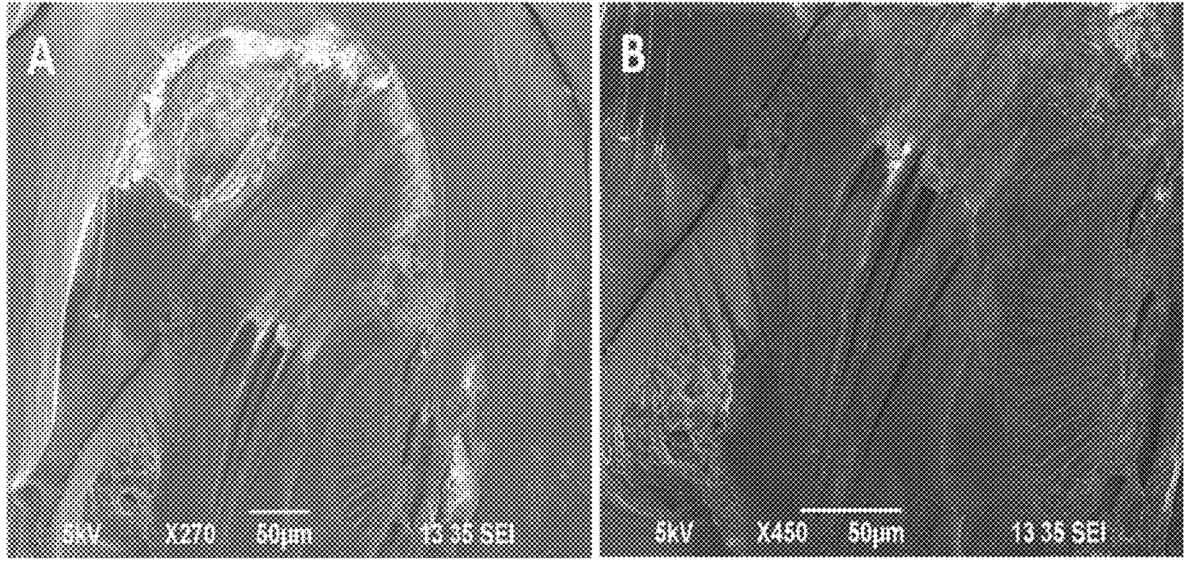
FIG. 10A-B is a series of images depicting SEM micrographs of antibiotic-releasing hemostatic agents. Ceftazidime hemostatic agent at 270× (A) and 450× magnifications (B).

SEM micrographs of the prepared hemostatic agents containing ceftazidime are shown in FIG. 10. Upon examination of the surface features of the hemostatic agents, a compact glassy layered morphology was seen. Ceftazidime hemostatic agents demonstrate a smoother morphology similar to that of the daptomycin hemostatic agents (FIG. 2). This is likely due to the increased reactivity of smaller antibiotics such as ciprofloxacin, ceftazidime, and ceftibuten. Reactions including these smaller structures were exothermic and literally hot to the touch when combined with EDC and gelatin. The smaller structure may yield increased rates of cephalosporin-gelatin conjugation and decreased rates of gelatin-gelatin conjugation.

Swelling Capacity of Antibiotic-Eluting Hemostatic Agents

Figure 11:
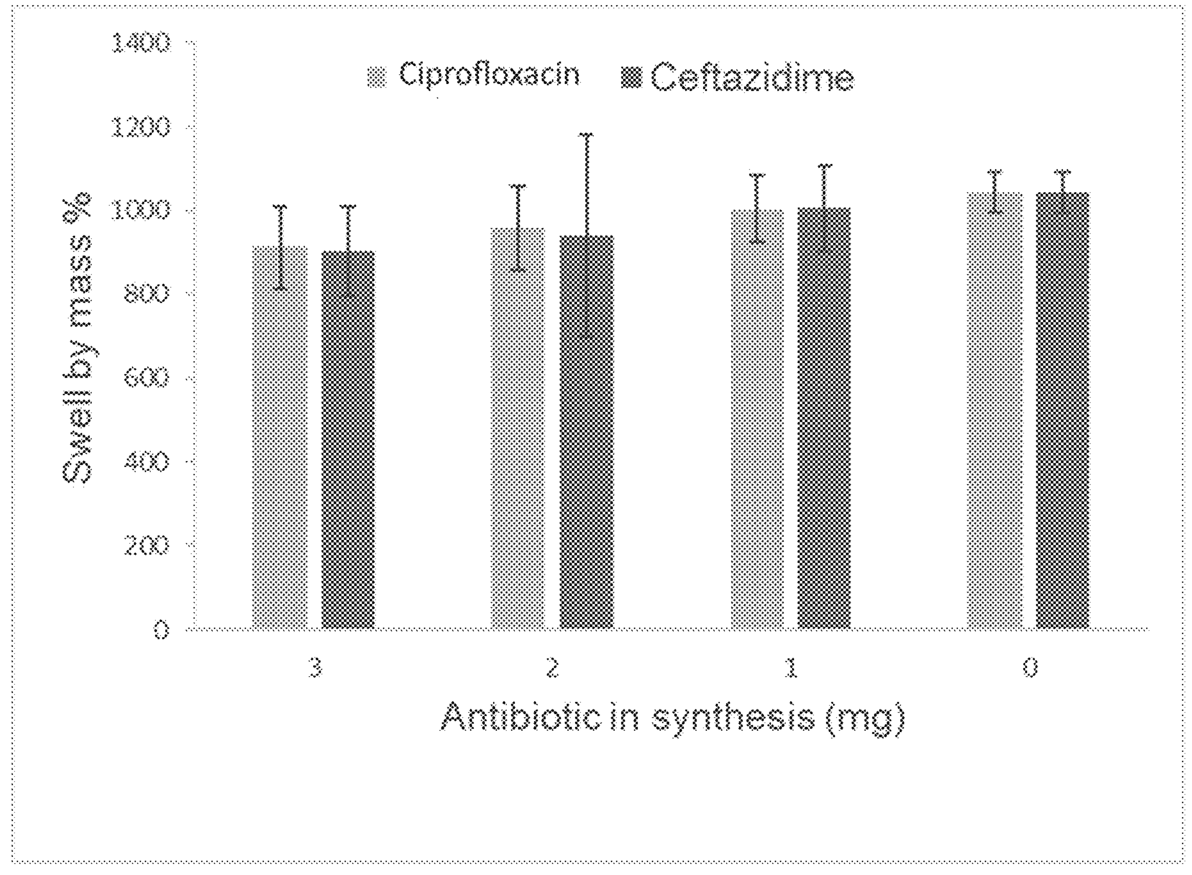
FIG. 11 is a graph depicting the swelling degree of antibiotic-eluting hemostatic agents. Each preparation was loaded with indicated antibiotic concentrations and allowed to swell for 24 hours. 0 mg of antibiotic used buffer in place of antibiotic for total volume and are reflective of cross-linked gelatin only.
Figure 12:
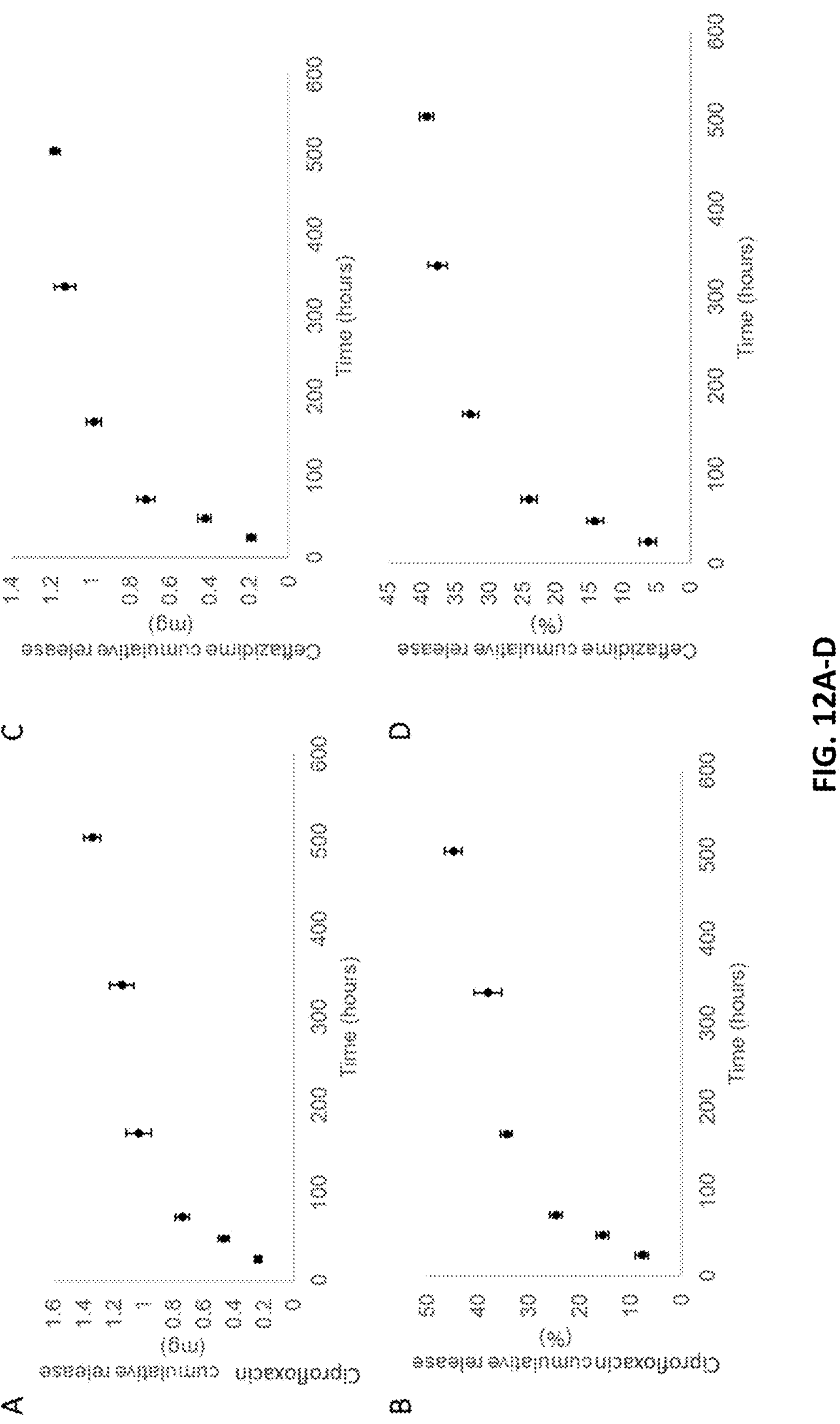
FIG. 12A-D are a series of graphs depicting in vitro release of antibiotic from antibiotic-eluting hemostatic agents. Each preparation was loaded with indicated antibiotic concentrations. (A & C) Cumulative release (mg) of ciprofloxacin and ceftazidime, respectively. (B & D) Cumulative release (%) of total antibiotic loaded in the hemostatic agent for ciprofloxacin and ceftazidime, respectively.

The swelling behavior of a hemostatic agent plays an important role in absorption of body fluids, metabolites, and regulating nutrients. FIG. 11 shows the swelling behavior of the antibiotic-eluting hemostatic agents with varying concentrations of antibiotic used for each. Compared with conjugated gelatin alone, both ciprofloxacin and ceftazidime conjugates had similar swelling profiles and swelling was decreased slightly by higher concentrations of antibiotic.

Antibiotic Release from Hemostatic Agents

Release profiles of ceftazidime-linked and ciprofloxacin-linked hemostatic agents determined by HPLC is shown in FIG. 12A-D. Ceftazidime and ciprofloxacin hemostatic agents showed steady and nearly equal release at earlier collection points up to 1 week. Following 1 week, slower release of ceftazidime and ciprofloxacin was sustained for over a period of 500 hours until separation was no longer practical.

Structure and Efficacy of Released Antibiotics from Hemostatic Agents

Figure 13:
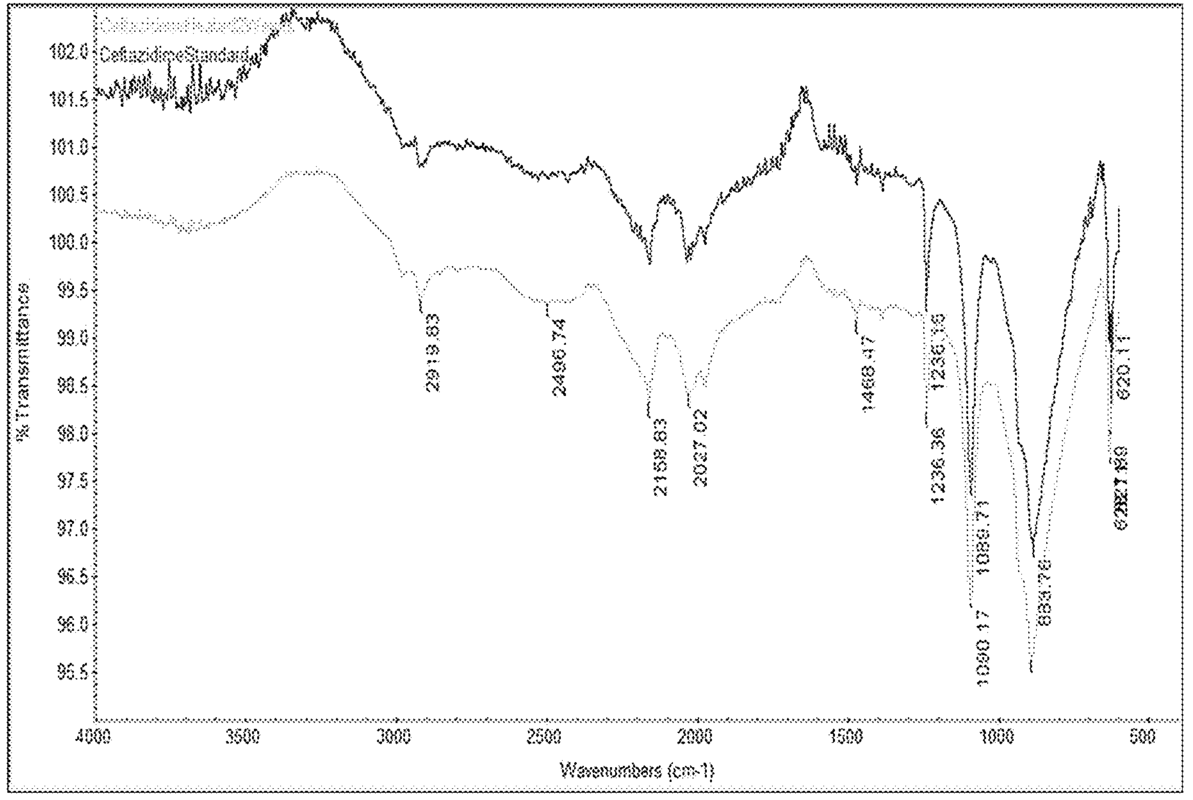
FIG. 13 is an image depicting FTIR spectra of antibiotic released from hemostatic agents. Pure ceftazidime standard was compared to samples released from hemostatic agents. Pure ceftazidime in dark grey, compared to samples released from the hemostatic agents after 2 weeks in light grey.
Figure 14:
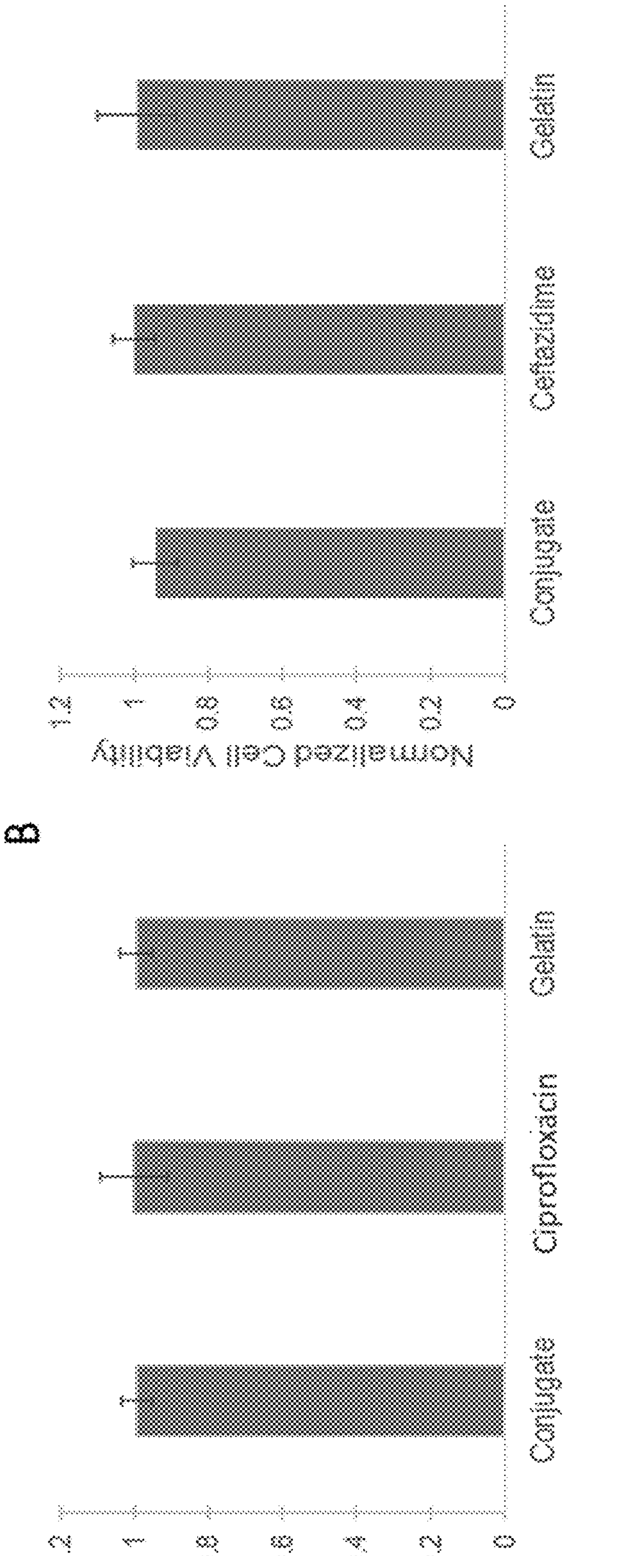
FIG. 14A-B are a series of graphs depicting normalized cell viability of fibroblasts in response to ciprofloxacin-eluting hemostatic agent samples (A) and ceftazidime-eluting hemostatic agent samples (B) from 48-hour release and controls including equivalent concentration of ciprofloxacin/ceftazidime and crosslinked gelatin.

Conjugation of antibiotics to gelatin via the activity of EDC may cause structural changes to the antibiotic itself. As such, FTIR spectral data was obtained of the released antibiotic samples. Basic chemical stability of ceftazidime was confirmed in all released samples as seen in the representative samples depicted in FIG. 13.

Biocompatibility of Antibiotics Released from Hemostatic Agents

Cell viability of human fibroblasts in the presence of the antibiotic-eluting hemostatic agents was assessed. Media incubated with prepared hemostatic agents containing released antibiotic was applied to cultured cells, as well as control concentrations of antibiotic, and media incubated with crosslinked gelatin.

Example 3—Non-Steroidal Anti-Inflammatory Drug (NSAID) Eluting Hemostatic Agents The NSAID-eluting hemostatic agent described herein provides for the continuous release of diclofenac for a minimum of 2 weeks. Similar to the antibiotic-eluting hemostatic agents described above, this functionality is accomplished through the use of carbodiimide chemistry to create crosslinked gelatin cages to entrap the NSAID for immediate and early delayed release while allowing for direct NSAID conjugation with gelatin, providing a sustained release.

Figure 15:
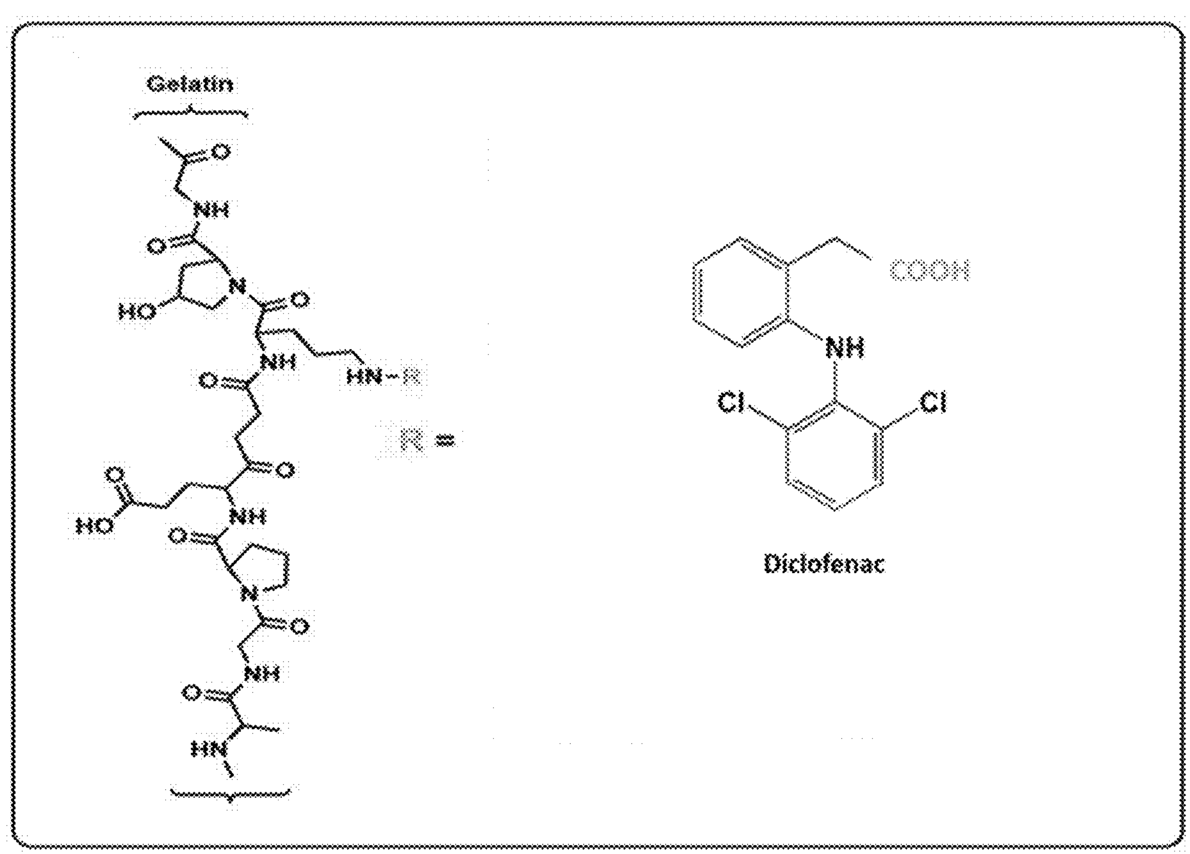
FIG. 15 is a schematic of gelatin conjugation with diclofenac. Gelatin structure is simplified to show representative amines that may form peptide bonds with the NSAID of interest when conjugated in the presence of EDC. The carboxylate group shown in grey on the diclofenac that may form a peptide bond with amine groups in gelatin.

As shown in FIG. 15, the degree of crosslinking between the gelatin and the NSAID is associated with the availability of carboxyl and amino functional groups on the NSAID. Hence, more available groups lead to additional conjugation (formation of amide bonds) between the gelatin and NSAID. Increased rates of amide bond formation between the NSAID and gelatin lead to slower release.

Materials and Methods

Materials

Gelatin type B, $Na_3PO_4$, diclofenac, 1-ethyl-3-(3-dimethylaminopropyl) carbodiimide (EDC), and absolute ethanol were purchased from Fisher Scientific (Waltham, MA). NaCl was purchased from Sigma-Aldrich (St. Louis, MO). HEK-293T fibroblasts were obtained from ATCC (Manassas, VA).

Preparation of Antibiotic-Eluting Hemostatic Agents

Gelatin was prepared as a 20 mg/mL stock solution in 0.1 M phosphate buffer at pH 7.4 with stirring at 50° C. until soluble. To prepare the conjugates, 20 mM carboxyl group concentration from the gelatin stock was incubated with diclofenac (1 mM) under activation by EDC (60 mM) for 2 hours at 50 rpm and 22° C. The product was precipitated under ice-cold absolute ethanol followed by centrifugation at 6000×g, then dissolved in 1.85 mM NaCl for washing, followed by a second round of precipitation. Conjugates were vacuum dried and heated at 80° C. to remove residual ethanol.

Antibiotic Release from Antibiotic-Eluting Hemostatic Agents

For release profile determination, conjugates were combined with 0.5 mL phosphate-buffered saline solution (PBS) to make a semisolid followed by immersion in 1 mL PBS. Samples were incubated at 37° C. and 100% relative humidity over a period of 2 weeks with 1 mL of PBS removed and then replaced with fresh PBS at 24, 48, 120, 168, and 336 hours. Release samples were stored at −80° C. until analysis to determine drug release kinetics of the conjugates. Release samples were filtered through syringe filters (0.45 m) and were analyzed by high performance liquid chromatography (Waters HPLC, 1100 series) to determine antibiotic concentrations. Samples were run for 10 min using 70/30 PBS/methanol mobile phase, 1 mL/min flow rate with a 150 L injection volume on a C18 reverse phase column (Supelco) coupled with UV detection (276 for diclofenac). Peak height was correlated with standards of known concentrations of the perspective antibiotic used in the conjugate to determine antibiotic concentration in the released samples.

Results

Characterization of Antibiotic-Eluting Hemostatic Agents

Crosslinking reactions performed in the presence of diclofenac allowed for the trapping of the non-steroidal anti-inflammatory drug (NSAID) in cage-like, crosslinked gelatin structures in addition to the direct conjugation of the NSAID to the gelatin. Possible binding outcomes of diclofenac with gelatin are illustrated in FIG. 15.

Hemostatic Agents

Release profiles of diclofenac-linked hemostatic agents determined by HPLC is shown in FIG. 16. Diclofenac conjugates showed steady and nearly equal release of diclofenac over the course of two weeks until separation was no longer practical. Due to the lack of additional functional groups available in the diclofenac to bind directly to the gelatin, it is likely that the diclofenac is sequestered in gelatin cages formed during the crosslinking reaction.

Example 4—In Vivo Prophetic Example—Vancomycin

A 40-year-old female patient undergoes spinal surgery. An antibiotic-eluting hemostatic agent is prepared using the following steps. Gelatin is prepared as a 20 mg/mL stock solution in 0.05 M MES buffer pH 5.0 with stirring at 50° C. until soluble. To prepare the hemostatic agents, 20 mM carboxyl group concentration from the gelatin stock is incubated with vancomycin (2.07 mM) under activation by EDC (60 mM) for 2 hours at 50 rpm and 22° C. The product is precipitated under ice-cold absolute ethanol followed by centrifugation at 6000×g, then dissolved in 1.85 mM NaCl for washing, followed by a second round of precipitation. Hemostatic agents are vacuum dried and heated at 80° C. to remove residual ethanol. The hemostatic agents are in a powder form after heating. Hemostatic agents are sterilized prior to administration to the patient by gamma or ultraviolet irradiation.

The antibiotic-eluting hemostatic agent containing vancomycin is applied to the surgical site to prevent infection before stitches are used to close the surgical wound site. The antibiotic is both immediately released from the hemostatic agent as well as sustainably released over a 3-week period to prevent infection. The patient's wound shows no signs of infection after 3 weeks. If needed, the hemostatic agent is reapplied. Alternatively, the hemostatic agent could be initially applied after stitches are placed.

Example 5—In Vivo Prophetic Example—Ciprofloxacin

A 36-year-old male patient undergoes surgery to his leg. An antibiotic-eluting hemostatic agent is prepared using the following steps. Gelatin is prepared as a 20 mg/mL stock solution in 0.05 M MES buffer pH 5.0 with stirring at 50° C. until soluble. To prepare the hemostatic agents, 20 mM carboxyl group concentration from the gelatin stock is incubated with ciprofloxacin (0.19 mM) under activation by EDC (60 mM) for 2 hours at 50 rpm and 22° C. The product is precipitated under ice-cold absolute ethanol followed by centrifugation at 6000×g, then dissolved in 1.85 mM NaCl for washing, followed by a second round of precipitation. Hemostatic agents are vacuum dried and heated at 80° C. to remove residual ethanol. The hemostatic agents are in a powder form after heating. Hemostatic agents are sterilized prior to administration to the patient by gamma or ultraviolet irradiation.

The antibiotic-eluting hemostatic agent containing ciprofloxacin is applied to the surgical site to prevent infection after stitches are placed. The antibiotic is both immediately released from the hemostatic agent as well as sustainably released over a 3-week period to prevent infection. The patient's wound shows no signs of infection after 3 weeks. If needed, the hemostatic agent is reapplied. Alternatively, the hemostatic agent could be initially applied before stitches are used to close the surgical wound site.

Example 6—In Vivo Prophetic Example—Diclofenac

A 50-year-old male patient undergoes surgery to his arm. An NSAID-eluting hemostatic agent is prepared using the following steps. Gelatin is prepared as a 20 mg/mL stock solution in 0.1 M phosphate buffer having a pH of 7.4 with stirring at 50° C. until soluble. To prepare the hemostatic agents, 20 mM carboxyl group concentration from the gelatin stock is incubated with diclofenac (1 mM) under activation by EDC (60 mM) for 2 hours at 50 rpm and 22° C. The product is precipitated under ice-cold absolute ethanol followed by centrifugation at 6000×g, then dissolved in 1.85 mM NaCl for washing, followed by a second round of precipitation. Hemostatic agents are vacuum dried and heated at 80° C. to remove residual ethanol. The hemostatic agents are in a powder form after heating. Hemostatic agents are sterilized prior to administration to the patient by gamma or ultraviolet irradiation.

The NSAID-eluting hemostatic agent containing diclofenac is applied to the surgical site to prevent inflammation after stitches are placed. The NSAID is both immediately released from the hemostatic agent as well as sustainably released over a 2-week period to prevent infection and decrease pain. The patient's wound shows no signs of inflammation after 2 weeks. If needed, the hemostatic agent is reapplied. Alternatively, the hemostatic agent could be initially applied before stitches are used to close the surgical wound site.

CONCLUSION

The inventors have developed a novel methodology for the controlled release of antibiotics and NSAIDs from active agent-eluting hemostatic agents. Through EDC-catalyzed conjugation, antibiotics and NSAIDs were successfully entrapped within gelatinous "cages" as well as directly conjugated to gelatin. The active agent-eluting hemostatic agents produced herein can be instrumental in antimicrobial prophylaxis and reducing inflammation and pain following surgery to help lower rates of surgical site infections and reduce unnecessary systemic administration of antibiotics or anti-inflammatories. This methodology can be further utilized to develop an assortment of products including bandages, suture replacements, and additional hemostatic agents which require a slow release of drugs that exhibit the required functional groups.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method of manufacturing an active agent-eluting hemostatic agent consisting of:

(a) preparing a solution of gelatin consisting essentially of gelatin type B and a buffer wherein the gelatin is present in the solution at about 2 wt. %;

(b) isolating a portion of the gelatin solution wherein the isolated portion has a carboxyl group concentration of about 20 mM;

(c) incubating and mixing at least one active agent, having at least one amine or carboxylate group in its structure, and a crosslinking agent with the isolated carboxyl group concentration for between about 1 hour to about 24 hours to allow complete crosslinking to form a product;

(d) precipitating the product of step (c) subsequent to the complete crosslinking;

(e) centrifuging the product of step (d), (f) subsequently washing the product from step (e) in sodium chloride;

(h) drying and heating the product of step (g) to form the active agent-eluting hemostatic agent; and (i) subsequently adding an amount of phosphate buffered saline to the product to achieve a paste-like consistency;

wherein the product is a macroscopic product having a compact, non-spherical, glassy layered morphology;

wherein the macroscopic product is not a powder;

wherein the at least one active agent is an anesthetic, an antimicrobial or combinations thereof.

2. The method of claim 1, wherein the crosslinking agent is 1-ethyl-3-(3-dimethylaminopropyl) carbodiimide (EDC) at a concentration between about 20 mM to about 60 mM.

3. The method of claim 1, wherein the at least one active agent is an antimicrobial selected from a group consisting of glycopeptide antibiotics, lipopeptide antibiotics, quinolones, and cephalosporins.

4. The method of claim 1, wherein the antibiotic is selected from the group consisting of vancomycin, daptomycin, ceftazidime, ciprofloxacin, and ceftibuten.

5. The method of claim 1, wherein the buffer is 2-(N-morpholino)ethanesulfonic acid (MES) buffer or NaHCO.

6. A method of manufacturing an active agent-eluting hemostatic agent consisting of:

(a) preparing a solution of gelatin consisting essentially of gelatin type B and a buffer wherein the gelatin is present in the solution at about 2 wt %;

(b) isolating a portion of the gelatin solution wherein the isolated portion has a carboxyl group concentration of about 20 mM;

(c) incubating and mixing at least one active agent, having at least one amine or carboxylate group in its structure, and a crosslinking agent with the isolated carboxyl group concentration for between about 1 hour to about 24 hours to allow complete crosslinking to form a product;

(d) precipitating the product of step (c) subsequent to the complete crosslinking;

(e) centrifuging the product of step (d);

(f) subsequently washing the product from step (e) in sodium chloride;

(g) precipitating the product of step (f);

(h) drying and heating the product of step (g) to form the active agent-eluting hemostatic agent;

wherein the product is a macroscopic product.

7. The method of claim 6, wherein the crosslinking agent is 1-ethyl-3-(3-dimethylaminopropyl) carbodiimide (EDC) at a concentration between about 20 mM to about 60 mM.

8. The method of claim 6, wherein the at least one active agent is an anesthetic, and antimicrobial, or combinations thereof.

9. The method of claim 6, wherein the at least one active agent is an antimicrobial selected from a group consisting of glycopeptide antibiotics, lipopeptide antibiotics, quinolones, and cephalosporins.

10. The method of claim 9, wherein the antibiotic is selected from the group consisting of vancomycin, daptomycin, ceftazidime, ciprofloxacin, and ceftibuten.

11. The method of claim 6, wherein the buffer is 2-(N-morpholino)ethanesulfonic acid (MES) buffer or NaHCO.

12. The method of claim 6, wherein the active agent-eluting hemostatic agent is in the form of a macroscopic powder.

* * * * *